United States Patent
Nair et al.

(10) Patent No.: US 7,402,415 B2
(45) Date of Patent: Jul. 22, 2008

(54) METHOD FOR THE PRODUCTION OF GLYCEROL BY RECOMBINANT ORGANISMS

(75) Inventors: Ramesh Nair, Wilmington, DE (US); Mark S. Payne, Wilmington, DE (US); Donald E. Trimbur, Redwood City, CA (US); Fernando Valle, Burlingame, CA (US)

(73) Assignees: E.I. du Pont de Nemours and Company, Wilmington, DE (US); Genencor International, Palo Alto, CA (US)

( * ) Notice: Subject to any disclaimer, the term of this patent is extended or adjusted under 35 U.S.C. 154(b) by 36 days.

(21) Appl. No.: 11/282,978

(22) Filed: Nov. 18, 2005

(65) Prior Publication Data
US 2006/0286653 A1 Dec. 21, 2006

Related U.S. Application Data

(60) Division of application No. 09/695,786, filed on Oct. 25, 2000, now Pat. No. 7,005,291, which is a division of application No. 08/982,783, filed on Dec. 2, 1997, now abandoned, which is a continuation-in-part of application No. 08/968,418, filed on Nov. 12, 1997, now abandoned.

(60) Provisional application No. 60/030,602, filed on Nov. 13, 1996.

(51) Int. Cl.
*C12P 7/18* (2006.01)
*C12P 7/20* (2006.01)
*C12N 9/02* (2006.01)
*C12N 1/21* (2006.01)
*C12N 15/74* (2006.01)

(52) U.S. Cl. ............... 435/159; 435/252.3; 435/194; 435/189; 435/69.1; 435/254.1; 435/255.1; 435/255.2; 435/252.1; 536/23.2

(58) Field of Classification Search ............... None
See application file for complete search history.

(56) References Cited

U.S. PATENT DOCUMENTS

| 6,358,716 B1 | 3/2002 | Bulthuis et al. |
| 6,514,733 B1 | 2/2003 | Laffend et al. |

FOREIGN PATENT DOCUMENTS

| FR | 2725145 A1 | 12/1996 |
| WO | 9635796 A1 | 8/1996 |
| WO | 9635795 A1 | 11/1996 |
| WO | 9635799 A1 | 11/1996 |
| WO | 9641888 A1 | 12/1996 |
| WO | 9707199 A1 | 2/1997 |
| WO | 9821339 A1 | 5/1998 |
| WO | 9821340 A1 | 5/1998 |
| WO | 9821341 A2 | 5/1998 |

OTHER PUBLICATIONS

Ben-Amotz et al., Experientia, vol. 38:49-52, 1982.
Albertyn et al, Mol. Cell Biol., vol. 14:4135-4144, 1994.
Hwa-Tang Wang et al., Cloning, Sequence, and Disruption of the *Saccharomyces diastaticus* Dar1 Gene Encoding a Glycerol-3-Phosphate Dehydrogenase, Journal of Bacteriology, vol. 176(22):7091-7095, 1994.
Hirayama et al., Cloning and Characterization of Seven CDNAS for Hyperosmolarity-Responsive (HOR) Genes of *Saccharomyces*, Mol. Gen. Genet., vol. 249:127-138, 1995.
Omori et al., Breeding of High Glycerol-Producing Shochu Yeast (*Sacchromyces cerevisiae*) with Acquired Salt Tolerance. Journal of Fermentation and Bioengineering, vol. 79:560-565, 1995.
Larason et al., A Gene Encoding SN-Glycerol 3-Phosphate Dehydrogenase (NAD+) Complements an Osmosensitive Mutant of *Saccharomyces cerevisiae*, Mol. Microbiol., vol. 10:1101, 1993.
Eustace, R. et al., Department of Microbiology and Genetics, Selective Hybridization and Wine Yeast for Higher Yields of Glycerol.
Norbeck et al., Purification and Characterization of Two Isoenzymes of DL-Glycerol-3-Phosphatase from *Saccharomyces cerevisiae*, J. Biol. Chem., vol. 271:13875, 1996.
Can. J. Microbiol., vol. 33:112-117, 1987.

*Primary Examiner*—Tekchand Saidha
*Assistant Examiner*—Younus Meah
(74) *Attorney, Agent, or Firm*—Christine M. Lhulier

(57) ABSTRACT

Recombinant organisms are provided comprising genes encoding a glycerol-3-phosphate dehydrogenase and/or a glycerol-3-phosphatase activity useful for the production of glycerol from a variety of carbon substrates. The organisms further contain disruptions in the endogenous genes encoding proteins having glycerol kinase and glycerol dehydrogenase activities.

7 Claims, 1 Drawing Sheet

METHOD FOR THE PRODUCTION OF GLYCEROL BY RECOMBINANT ORGANISMS

Figure 1:
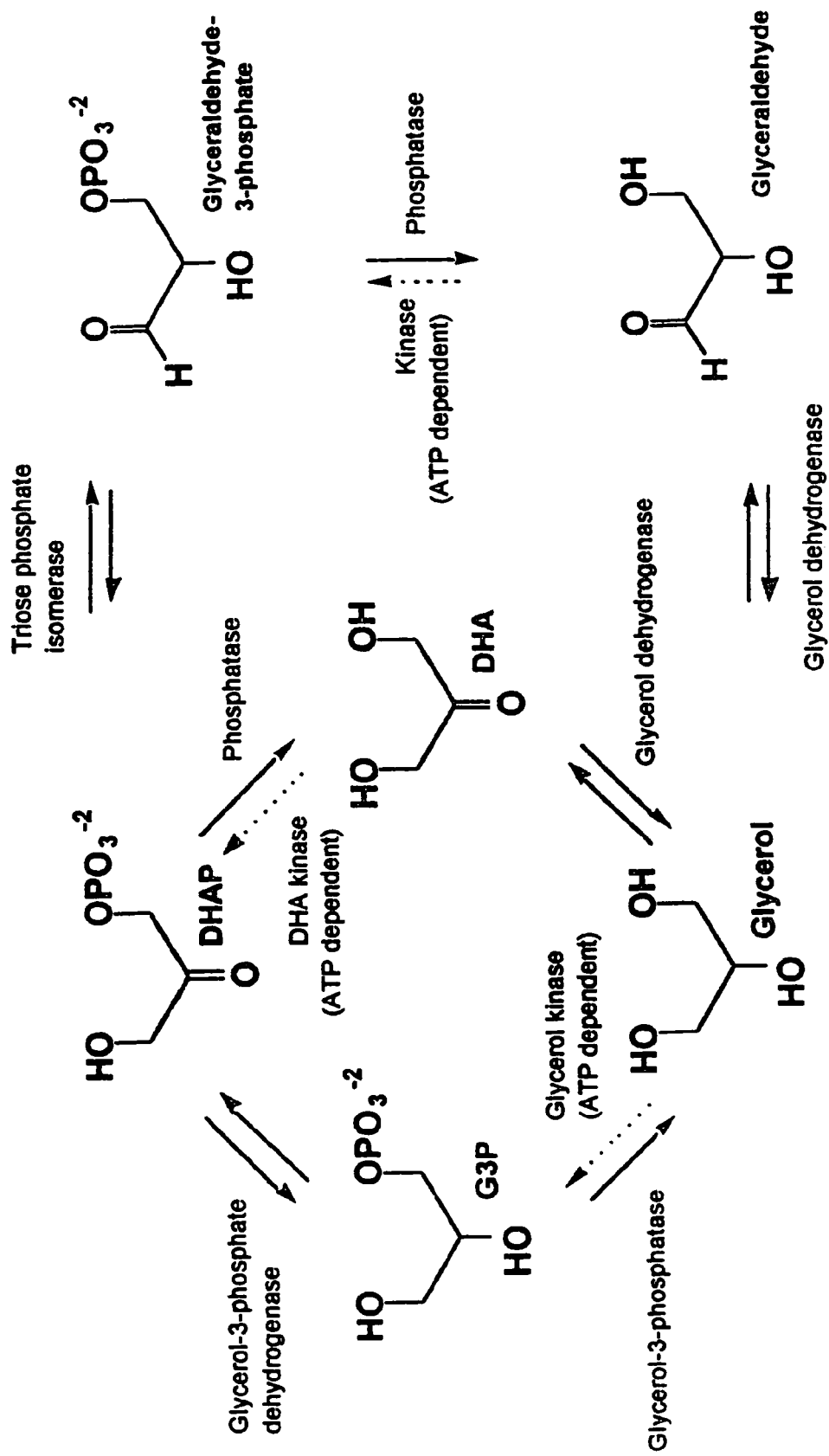

This application is a divisional of U.S. application Ser. No. 09/695,786, which is a divisional of U.S. application Ser. No. 08/982,783 filed 2 Dec. 1997 (now abandoned), which is a continuation-in-part of U.S. application Ser. No. 08/968,418 filed 12 Nov. 1997, (now abandoned), claiming benefit to U.S. Provisional Application No. 60/030,602, filed 13 Nov. 1996.

FIELD OF INVENTION

The present invention relates to the field of molecular biology and the use of recombinant organisms for the production of glycerol and compounds derived from the glycerol biosynthetic pathway. More specifically the invention describes the construction of a recombinant cell for the production of glycerol and derived compounds from a carbon substrate, the cell containing foreign genes encoding proteins having glycerol-3-phosphate dehydrogenase (G3PDH) and glycerol-3-phosphatase (G3P phosphatase) activities where the endogenous genes encoding the glycerol-converting glycerol kinase and glycerol dehydrogenase activities have been deleted.

BACKGROUND

Glycerol is a compound in great demand by industry for use in cosmetics, liquid soaps, food, pharmaceuticals, lubricants, anti-freeze solutions, and in numerous other applications. The esters of glycerol are important in the fat and oil industry. Historically, glycerol has been isolated from animal fat and similar sources; however, the process is laborious and inefficient. Microbial production of glycerol is preferred.

Not all organisms have a natural capacity to synthesize glycerol. However, the biological production of glycerol is known for some species of bacteria, algae, and yeast. The bacteria *bacillus licheniformis* and *Lactobacillus lycopersica* synthesize glycerol. Glycerol production is found in the halotolerant algae *Dunaliella* sp. and *Asteromonas gracilis* for protection against high external salt concentrations (Ben-Amotz et al., (1982) *Experientia* 38:49-52). Similarly, various osmotolerant yeast synthesize glycerol as a protective measure. Most strains of *Saccharomyces* produce some glycerol during alcoholic fermentation and this production can be increased by the application of osmotic stress (Albertyn et al., (1994) *Mol. Cell. Biol.* 14, 4135-4144). Earlier this century glycerol was produced commercially with *Saccharomyces* cultures to which steering reagents were added such as sulfites or alkalis. Through the formation of an inactive complex, the steering agents block or inhibit the conversion of acetaldehyde to ethanol; thus, excess reducing equivalents (NADH) are available to or "steered" towards dihydroxyacetone phosphate (DHAP) for reduction to produce glycerol. This method is limited by the partial inhibition of yeast growth that is due to the sulfites. This limitation can be partially overcome by the use of alkalis which create excess NADH equivalents by a different mechanism. In this practice, the alkalis initiated a Cannizarro disproportionation to yield ethanol and acetic acid from two equivalents of acetaldehyde. Thus, although production of glycerol is possible from naturally occurring organisms, production is often subject to the need to control osmotic stress of the cultures and the production of sulfites. A method free from these limitations is desirable. Production of glycerol from recombinant organisms containing foreign genes encoding key steps in the glycerol biosynthetic pathway is one possible route to such a method.

A number of the genes involved in the glycerol biosynthetic pathway have been isolated. For example, the gene encoding glycerol-3-phosphate dehydrogenase (DAR1, GPD1) has been cloned and sequenced from *Saccharomyces diastaticus* (Wang et al., (1994), *J. Bact.* 176:7091-7095). The DAR1 gene was cloned into a shuttle vector and used to transform *E. coli* where expression produced active enzyme. Wang et al., supra, recognizes that DAR1 is regulated by the cellular osmotic environment but does not suggest how the gene might be used to enhance glycerol production in a recombinant organism.

Other glycerol-3-phosphate dehydrogenase enzymes have been isolated. For example, sn-glycerol-3-phosphate dehydrogenase has been cloned and sequenced from *S. cerevisiae* (Larason et al., (1993) *Mol. Microbiol.*, 10:1101). Albertyn et al., (1994) *Mol. Cell. Biol.*, 14:4135) teach the cloning of GPD1 encoding a glycerol-3-phosphate dehydrogenase from *S. cerevisiae*. Like Wang et al., both Albertyn et al. and Larason et al. recognize the osmo-sensitvity of the regulation of this gene but do not suggest how the gene might be used in the production of glycerol in a recombinant organism.

As with G3PDH, glycerol-3-phosphatase has been isolated from *Saccharomyces cerevisiae* and the protein identified as being encoded by the GPP1 and GPP2 genes (Norbeck et al., (1996) *J. Biol. Chem.*, 271:13875). Like the genes encoding G3PDH, it appears that GPP2 is osmotically-induced.

Although the genes encoding G3PDH and G3P phosphatase have been isolated, there is no teaching in the art that demonstrates glycerol production from recombinant organisms with G3PDH/G3P phosphatase expressed together or separately. Further, there is no teaching to suggest that efficient glycerol production from any wild-type organism is possible using these two enzyme activities that does not require applying some stress (salt or an osmolyte) to the cell. In fact, the art suggests that G3PDH activities may not affect glycerol production. For example, Eustace ((1987), *Can. J. Microbiol.*, 33:112-117)) teaches hybridized yeast strains that produced glycerol at greater levels than the parent strains. However, Eustace also demonstrates that G3PDH activity remained constant or slightly lower in the hybridized strains as opposed to the wild type.

Glycerol is an industrially useful material. However, other compounds may be derived from the glycerol biosynthetic pathway that also have commercial significance. For example, glycerol-producing organisms may be engineered to produce 1,3-propanediol (U.S. Pat. No. 5,686,276), a monomer having potential utility in the production of polyester fibers and the manufacture of polyurethanes and cyclic compounds. It is known for example that in some organisms, glycerol is converted to 3-hydroxypropionaldehyde and then to 1,3-propanediol through the actions of a dehydratase enzyme and an oxidoreductase enzyme, respectively. Bacterial strains able to produce 1,3-propanediol have been found, for example, in the groups *Citrobacter, Clostridium, Enterobacter, Ilyobacter, Klebsiella, Lactobacillus*, and *Pelobacter*. Glycerol dehydratase and diol dehydratase systems are described by Seyfried et al. (1996) *J. Bacteriol.* 178:5793-5796 and Tobimatsu et al. (1995) *J. Biol. Chem.* 270:7142-7148, respectively. Recombinant organisms, containing exogenous dehydratase enzyme, that are able to produce 1,3-propanediol have been described (U.S. Pat. No. 5,686,276). Although these organisms produce 1,3-propanediol, it is clear that they would benefit from a system that would minimize glycerol conversion.

There are a number of advantages in engineering a glycerol-producing organism for the production of 1,3-propanediol where conversion of glycerol is minimized. A microorganism capable of efficiently producing glycerol under physiological conditions is industrially desirable, especially when the glycerol itself will be used as a substrate in vivo as part of a more complex catabolic or biosynthetic pathway that could be perturbed by osmotic stress or the addition of steering agents (e.g., the production of 1,3-propanediol). Some attempts at creating glycerol kinase and glycerol dehydrogenase mutants have been made. For example, De Koning et al. (1990) *Appl. Microbiol Biotechnol.* 32:693-698 report the methanol-dependent production of dihydroxyacetone and glycerol by mutants of the methylotrophic yeast *Hansenula polymorpha* blocked in dihydroxyacetone kinase and glycerol kinase. Methanol and an additional substrate, required to replenish the xyulose-5-phosphate co-substrate of the assimilation reaction, were used to produce glycerol; however, a dihydroxyacetone reductase (glycerol dehydrogenase) is also required. Similarly, Shaw and Cameron, Book of Abstracts, 211th ACS National Meeting, New Orleans, La., Mar. 24-28 (1996), BIOT-154 Publisher: American Chemical Society, Washington, D.C., investigate the deletion of ldhA (lactate dehydrogenase), glpK (glycerol kinase), and tpiA (triosephosphate isomerase) for the optimization of 1,3-propanediol production. They do not suggest the expression of cloned genes for G3PDH or G3P phosphatase for the production of glycerol or 1,3-propanediol and they do not discuss the impact of glycerol dehydrogenase.

The problem to be solved, therefore, is the lack of a process to direct carbon flux towards glycerol production by the addition or enhancement of certain enzyme activities, especially G3PDH and G3P phosphatase which respectively catalyze the conversion of dihydroxyacetone phosphate (DHAP) to glycerol-3-phosphate (G3P) and then to glycerol. The problem is complicated by the need to control the carbon flux away from glycerol by deletion or decrease of certain enzyme activities, especially glycerol kinase and glycerol dehydrogenase which respectively catalyze the conversion of glycerol plus ATP to G3P and glycerol to dihydroxyacetone (or glyceraldehyde).

SUMMARY OF THE INVENTION

The present invention provides a method for the production of glycerol from a recombinant organism comprising: transforming a suitable host cell with an expression cassette comprising either one or both of (a) a gene encoding a protein having glycerol-3-phosphate dehydrogenase activity and (b) a gene encoding a protein having glycerol-3-phosphate phosphatase activity, where the suitable host cell contains a disruption in either one or both of (a) a gene encoding an endogenous glycerol kinase and (b) a gene encoding an endogenous glycerol dehydrogenase, wherein the disruption prevents the expression of active gene product; culturing the transformed host cell in the presence of at least one carbon source selected from the group consisting of monosaccharides, oligosaccharides, polysaccharides, and single-carbon substrates, whereby glycerol is produced; and recovering the glycerol produced.

The present invention further provides a process for the production of 1,3-propanediol from a recombinant organism comprising: transforming a suitable host cell with an expression cassette comprising either one or both of (a) a gene encoding a protein having glycerol-3-phosphate dehydrogenase activity and (b) a gene encoding a protein having glycerol-3-phosphate phosphatase activity, the suitable host cell having at least one gene encoding a protein having a dehydratase activity and having a disruption in either one or both of (a) a gene encoding an endogenous glycerol kinase and (b) a gene encoding an endogenous glycerol dehydrogenase, wherein the disruption in the genes of (a) or (b) prevents the expression of active gene product; culturing the transformed host cell in the presence of at least one carbon source selected from the group consisting of monosaccharides, oligosaccharides, polysaccharides, and single-carbon substrates whereby 1,3-propanediol is produced; and recovering the 1,3-propanediol produced.

Additionally, the invention provides for a process for the production of 1,3-propanediol from a recombinant organism where multiple copies of endogeneous genes are introduced.

Further embodiments of the invention include host cells transformed with heterologous genes for the glycerol pathway as well as host cells which contain endogeneous genes for the glycerol pathway.

Additionally, the invention provides recombinant cells suitable for the production either glycerol or 1,3-propanediol, the host cells having genes expressing either one or both of a glycerol-3-phosphate dehydrogenase activity and a glycerol-3-phosphate phosphatase activity wherein the cell also has disruptions in either one or both of a gene encoding an endogenous glycerol kinase and a gene encoding an endogenous glycerol dehydrogenase, wherein the disruption in the genes prevents the expression of active gene product.

BRIEF DESCRIPTION OF THE FIGURES, BIOLOGICAL DEPOSITS AND SEQUENCE LISTING

FIG. 1 illustrates the representative enzymatic pathways involving glycerol metabolism.

Applicants have made the following biological deposits under the terms of the Budapest Treaty on the International Recognition of the Deposit of Micro-organisms for the Purposes of Patent Procedure:

| Depositor Identification Reference | Int'l. Depository Designation | Date of Deposit |
|---|---|---|
| *Escherichia coli* pAH21/DH5α (containing the GPP2 gene) | ATCC 98187 | 26 Sep. 1996 |
| *Escherichia coli* (pDAR1A/AA200) (containing the DAR1 gene) | ATCC 98248 | 6 Nov. 1996 |
| FM5 *Escherichia coli* RJF10m (containing a glpK disruption) | ATCC 98597 | 25 Nov. 1997 |
| FM5 *Escherichia coli* MSP33.6 (containing a gldA disruption) | ATCC 98598 | 25 Nov. 1997 |

"ATCC" refers to the American Type Culture Collection international depository located at 10801 University Blvd. Manassas, Va. 20110-2209 U.S.A. The designation is the accession number of the deposited material.

Applicants have provided 43 sequences in conformity with the Rules for the Standard Representation of Nucleotide and Amino Acid Sequences in Patent Applications (Annexes I and II to the Decision of the President of the EPO, published in Supplement No. 2 to OJ EPO, 12/1992) and with 37 C.F.R. 1.821-1.825 and Appendices A and B (Requirements for Application Disclosures Containing Nucleotides and/or Amino Acid Sequences).

DETAILED DESCRIPTION OF THE INVENTION

The present invention solves the problem stated above by providing a method for the biological production of glycerol from a fermentable carbon source in a recombinant organism.

The method provides a rapid, inexpensive and environmentally-responsible source of glycerol useful in the cosmetics and pharmaceutical industries. The method uses a microorganism containing cloned homologous or heterologous genes encoding glycerol-3-phosphate dehydrogenase (G3PDH) and/or glycerol-3-phosphatase (G3P phosphatase). These genes are expressed in a recombinant host having disruptions in genes encoding endogenous glycerol kinase and/or glycerol dehydrogenase enzymes. The method is useful for the production of glycerol, as well as any end products for which glycerol is an intermediate. The recombinant microorganism is contacted with a carbon source and cultured and then glycerol or any end products derived therefrom are isolated from the conditioned media. The genes may be incorporated into the host microorganism separately or together for the production of glycerol.

Applicants' process has not previously been described for a recombinant organism and required the isolation of genes encoding the two enzymes and their subsequent expression in a host cell having disruptions in the endogenous kinase and dehydrogenase genes. It will be appreciated by those familiar with this art that Applicants' process may be generally applied to the production compounds where glycerol is a key intermediate, e.g., 1,3-propanediol.

As used herein the following terms may be used for interpretation of the claims and specification.

The terms "glycerol-3-phosphate dehydrogenase" and "G3PDH" refer to a polypeptide responsible for an enzyme activity that catalyzes the conversion of dihydroxyacetone phosphate (DHAP) to glycerol-3-phosphate (G3P). In vivo G3PDH may be NADH; NADPH; or FAD-dependent. The NADH-dependent enzyme (EC 1.1.1.8) is encoded, for example, by several genes including GPD1 (GenBank Z74071x2), or GPD2 (GenBank Z35169x1), or GPD3 (GenBank G984182), or DAR1 (GenBank Z74071x2). The NADPH-dependent enzyme (EC 1.1.1.94) is encoded by gpsA (GenBank U321643, (cds 197911-196892) G466746 and L45246). The FAD-dependent enzyme (EC 1.1.99.5) is encoded by GUT2 (GenBank Z47047x23), or glpD (GenBank G147838), or glpABC (GenBank M20938).

The terms "glycerol-3-phosphatase", "sn-glycerol-3-phosphatase", or "d,l-glycerol phosphatase", and "G3P phosphatase" refer to a polypeptide responsible for an enzyme activity that catalyzes the conversion of glycerol-3-phosphate and water to glycerol and inorganic phosphate. G3P phosphatase is encoded, for example, by GPP1 (GenBank Z47047x125), or GPP2 (GenBank U18813x11).

The term "glycerol kinase" refers to a polypeptide responsible for an enzyme activity that catalyzes the conversion of glycerol and ATP to glycerol-3-phosphate and ADP. The high energy phosphate donor ATP may be replaced by physiological substitutes (e.g. phosphoenolpyruvate). Glycerol kinase is encoded, for example, by GUTI (GenBank U11583x9) and glpK (GenBank LI 9201).

The term "glycerol dehydrogenase" refers to a polypeptide responsible for an enzyme activity that catalyzes the conversion of glycerol to dihydroxyacetone (E.C. 1.1.1.6) or glycerol to glyceraldehyde (E.C. 1.1.1.72). A polypeptide responsible for an enzyme activity that catalyzes the conversion of glycerol to dihydroxyacetone is also referred to as a "dihydroxyacetone reductase". Glycerol dehydrogenase may be dependent upon NADH (E.C. 1.1.1.6), NADPH (E.C. 1.1.1.72), or other cofactors (e.g., E.C. 1.1.99.22). A NADH-dependent glycerol dehydrogenase is encoded, for example, by gldA (GenBank U00006).

The term "dehydratase enzyme" will refer to any enzyme that is capable of isomerizing or converting a glycerol molecule to the product 3-hydroxypropion-aldehyde. For the purposes of the present invention the dehydratase enzymes include a glycerol dehydratase (E.C. 4.2.1.30) and a diol dehydratase (E.C. 4.2.1.28) having preferred substrates of glycerol and 1,2-propanediol, respectively. In *Citrobacter freundii*, for example, glycerol dehydratase is encoded by three polypeptides whose gene sequences are represented by dhaB, dhaC and dhaE (GenBank U09771: base pairs 8556-10223, 10235-10819, and 10822-11250, respectively). In *Klebsiella oxytoca*, for example, diol dehydratase is encoded by three polypeptides whose gene sequences are represented by pddA, pddB, and pddC (GenBank D45071: base pairs 121-1785, 1796-2470, and 2485-3006, respectively).

The terms "GPD1", "DAR1", "OSG1", "D2830", and "YDL022W" will be used interchangeably and refer to a gene that encodes a cytosolic glycerol-3-phosphate dehydrogenase and is characterized by the base sequence given as SEQ ID NO:1.

The term "GPD2" refers to a gene that encodes a cytosolic glycerol-3-phosphate dehydrogenase and is characterized by the base sequence given in SEQ ID NO:2.

The terms "GUT2" and "YIL155C" are used interchangeably and refer to a gene that encodes a mitochondrial glycerol-3-phosphate dehydrogenase and is characterized by the base sequence given in SEQ ID NO:3.

The terms "GPP1", "RHR2" and "YIL053W" are used interchangeably and refer to a gene that encodes a cytosolic glycerol-3-phosphatase and is characterized by the base sequence given in SEQ ID NO:4.

The terms "GPP2", "HOR2" and "YER062C" are used interchangeably and refer to a gene that encodes a cytosolic glycerol-3-phosphatase and is characterized by the base sequence given as SEQ ID NO:5.

The term "GUT1" refers to a gene that encodes a cytosolic glycerol kinase and is characterized by the base sequence given as SEQ ID NO:6. The term "glpK" refers to another gene that encodes a glycerol kinase and is characterized by the base sequence given in GeneBank L19201, base pairs 77347-78855.

The term "gldA" refers to a gene that encodes a glycerol dehydrogenase and is characterized by the base sequence given in GeneBank U00006, base pairs 3174-4316. The term "dhaD" refers to another gene that encodes a glycerol dehydrogenase and is characterized by the base sequence given in GeneBank U09771, base pairs 2557-3654.

As used herein, the terms "function" and "enzyme function" refer to the catalytic activity of an enzyme in altering the energy required to perform a specific chemical reaction. Such an activity may apply to a reaction in equilibrium where the production of both product and substrate may be accomplished under suitable conditions.

The terms "polypeptide" and "protein" are used interchangeably.

The terms "carbon substrate" and "carbon source" refer to a carbon source capable of being metabolized by host organisms of the present invention and particularly mean carbon sources selected from the group consisting of monosaccharides, oligosaccharides, polysaccharides, and one-carbon substrates or mixtures thereof.

"Conversion" refers to the metabolic processes of an organism or cell that by means of a chemical reaction degrades or alters the complexity of a chemical compound or substrate.

The terms "host cell" and "host organism" refer to a microorganism capable of receiving foreign or heterologous genes and additional copies of endogeneous genes and expressing those genes to produce an active gene product.

The terms "production cell" and "production organism" refer to a cell engineered for the production of glycerol or compounds that may be derived from the glycerol biosynthetic pathway. The production cell will be recombinant and contain either one or both of a gene that encodes a protein having a glycerol-3-phosphate dehydrogenase activity and a gene encoding a protein having a glycerol-3-phosphatase activity. In addition to the G3PDH and G3P phosphatase genes, the host cell will contain disruptions in one or both of a gene encoding an endogenous glycerol kinase and a gene encoding an endogenous glycerol dehydrogenase. Where the production cell is designed to produce 1,3-propanediol, it will additionally contain a gene encoding a protein having a dehydratase activity.

The terms "foreign gene", "foreign DNA", "heterologous gene", and "heterologous DNA" all refer to genetic material native to one organism that has been placed within a different host organism.

The term "endogenous" as used herein with reference to genes or polypeptides expressed by genes, refers to genes or polypeptides that are native to a production cell and are not derived from another organism. Thus an "endogenous glycerol kinase" and an "endogenous glycerol dehydrogenase" are terms referring to polypeptides encoded by genes native to the production cell.

The terms "recombinant organism" and "transformed host" refer to any organism transformed with heterologous or foreign genes. The recombinant organisms of the present invention express foreign genes encoding G3PDH and G3P phosphatase for the production of glycerol from suitable carbon substrates. Additionally, the terms "recombinant organism" and "transformed host" refer to any organism transformed with endogenous (or homologous) genes so as to increase the copy number of the genes. "Gene" refers to a nucleic acid fragment that expresses a specific protein, including regulatory sequences preceding (5' non-coding) and following (3' non-coding) the coding region. The terms "native" and "wild-type" gene refer to the gene as found in nature with its own regulatory sequences.

The terms "encoding" and "coding" refer to the process by which a gene, through the mechanisms of transcription and translation, produces an amino acid sequence. The process of encoding a specific amino acid sequence is meant to include DNA sequences that may involve base changes that do not cause a change in the encoded amino acid, or which involve base changes which may alter one or more amino acids, but do not affect the functional properties of the protein encoded by the DNA sequence. Therefore, the invention encompasses more than the specific exemplary sequences. Modifications to the sequence, such as deletions, insertions, or substitutions in the sequence which produce silent changes that do not substantially affect the functional properties of the resulting protein molecule are also contemplated. For example, alterations in the gene sequence which reflect the degeneracy of the genetic code, or which result in the production of a chemically equivalent amino acid at a given site, are contemplated; thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a biologically equivalent product. Nucleotide changes which result in alteration of the N-terminal and C-terminal portions of the protein molecule would also not be expected to alter the activity of the protein. In some cases, it may in fact be desirable to make mutants of the sequence in order to study the effect of alteration on the biological activity of the protein. Each of the proposed modifications is well within the routine skill in the art, as is determination of retention of biological activity in the encoded products. Moreover, the skilled artisan recognizes that sequences encompassed by this invention are also defined by their ability to hybridize, under stringent conditions (0.1×SSC, 0.1% SDS, 65° C.), with the sequences exemplified herein.

The term "expression" refers to the transcription and translation to gene product from a gene coding for the sequence of the gene product.

The terms "plasmid", "vector", and "cassette" as used herein refer to an extra chromosomal element often carrying genes which are not part of the central metabolism of the cell and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements in addition to the foreign gene that facilitate transformation of a particular host cell. "Expression cassette" refers to a specific vector containing a foreign gene and having elements in addition to the foreign gene that allow for enhanced expression of that gene in a foreign host.

The terms "transformation" and "transfection" refer to the acquisition of new genes in a cell after the incorporation of nucleic acid. The acquired genes may be integrated into chromosomal DNA or introduced as extrachromosomal replicating sequences. The term "transformant" refers to the cell resulting from a transformation.

The term "genetically altered" refers to the process of changing hereditary material by transformation or mutation. The terms "disruption" and "gene interrupt" as applied to genes refer to a method of genetically altering an organism by adding to or deleting from a gene a significant portion of that gene such that the protein encoded by that gene is either not expressed or not expressed in active form.

Glycerol Biosynthetic Pathway

It is contemplated that glycerol may be produced in recombinant organisms by the manipulation of the glycerol biosynthetic pathway found in most microorganisms. Typically, a carbon substrate such as glucose is converted to glucose-6-phosphate via hexokinase in the presence of ATP. Glucose-phosphate isomerase catalyzes the conversion of glucose-6-phosphate to fructose-6-phosphate and then to fructose-1,6-diphosphate through the action of 6-phosphofructokinase. The diphosphate is then taken to dihydroxyacetone phosphate (DHAP) via aldolase. Finally NADH-dependent G3PDH converts DHAP to glycerol-3-phosphate which is then dephosphorylated to glycerol by G3P phosphatase. (Agarwal (1990), *Adv. Biochem. Engrg.* 41:114).

Genes Encoding G3PDH, Glycerol Dehydrogenase G3P Phosphatase and Glycerol Kinase The present invention provides genes suitable for the expression of G3PDH and G3P phosphatase activities in a host cell.

Genes encoding G3PDH are known. For example, GPD1 has been isolated from *Saccharomyces* and has the base sequence given by SEQ ID NO:1, encoding the amino acid sequence given in SEQ ID NO:7 (Wang et al., supra). Similarly, G3PDH activity has also been isolated from *Saccharomyces* encoded by GPD2 having the base sequence given in SEQ ID NO:2 encoding the amino acid sequence given in SEQ ID NO:8 (Eriksson et al., (1995) *Mol. Microbiol.*, 17:95).

For the purposes of the present invention it is contemplated that any gene encoding a polypeptide responsible for G3PDH activity is suitable wherein that activity is capable of catalyzing the conversion of dihydroxyacetone phosphate (DHAP) to glycerol-3-phosphate (G3P). Further, it is contemplated that any gene encoding the amino acid sequence of G3PDH as given by SEQ ID NOS:7, 8, 9, 10, 11 and 12 corresponding to the genes GPD1, GPD2, GUT2, gpsA, glpD, and the α subunit of glpABC respectively, will be functional in the present invention wherein that amino acid sequence may encompass amino acid substitutions, deletions or additions that do not alter the function of the enzyme. The skilled person will appreciate that genes encoding G3PDH isolated from other sources will also be suitable for use in the present invention. For example, genes isolated from prokaryotes include GenBank accessions M34393, M20938, L06231, U12567, L45246, L45323, L45324, L45325, U32164, U32689, and U39682. Genes isolated from fungi include GenBank accessions U30625, U30876 and X56162; genes isolated from insects include GenBank accessions X61223 and X14179; and genes isolated from mammalian sources include GenBank accessions U12424, M25558 and X78593.

Genes encoding G3P phosphatase are known. For example, GPP2 has been isolated from *Saccharomyces cerevisiae* and has the base sequence given by SEQ ID NO:5, which encodes the amino acid sequence given in SEQ ID NO:13 (Norbeck et al., (1996), *J. Biol. Chem.*, 271:13875).

For the purposes of the present invention, any gene encoding a G3P phosphatase activity is suitable for use in the method wherein that activity is capable of catalyzing the conversion of glycerol-3-phosphate and water to glycerol and inorganic phosphate. Further, any gene encoding the amino acid sequence of G3P phosphatase as given by SEQ ID NOS: 13 and 14 corresponding to the genes GPP2 and GPP1 respectively, will be functional in the present invention including any amino acid sequence that encompasses amino acid substitutions, deletions or additions that do not alter the function of the G3P phosphatase enzyme. The skilled person will appreciate that genes encoding G3P phosphatase isolated from other sources will also be suitable for use in the present invention. For example, the dephosphorylation of glycerol-3-phosphate to yield glycerol may be achieved with one or more of the following general or specific phosphatases: alkaline phosphatase (EC 3.1.3.1) [GenBank M19159, M29663, U02550 or M33965]; acid phosphatase (EC 3.1.3.2) [GenBank U51210, U19789, U28658 or L20566]; glycerol-3-phosphatase (EC 3.1.3.21) [GenBank Z38060 or U18813x11]; glucose-1-phosphatase (EC 3.1.3.10) [GenBank M33807]; glucose-6-phosphatase (EC 3.1.3.9) [GenBank U00445]; fructose-1,6-bisphosphatase (EC 3.1.3.11) [GenBank X12545 or J03207] or phosphotidyl glycero phosphate phosphatase (EC 3.1.3.27) [GenBank M23546 and M23628].

Genes encoding glycerol kinase are known. For example, GUT1 encoding the glycerol kinase from *Saccharomyces* has been isolated and sequenced (Pavlik et al. (1993), *Curr. Genet.*, 24:21) and the base sequence is given by SEQ ID NO:6, which encodes the amino acid sequence given in SEQ ID NO:15. Alternatively, glpK encodes a glycerol kinase from *E. coli* and is characterized by the base sequence given in GeneBank L19201, base pairs 77347-78855.

Genes encoding glycerol dehydrogenase are known. For example, gldA encodes a glycerol dehydrogenase from *E. coli* and is characterized by the base sequence given in GeneBank U00006, base pairs 3174-4316. Alternatively, dhaD refers to another gene that encodes a glycerol dehydrogenase from *Citrobacter freundii* and is characterized by the base sequence given in GeneBank U09771, base pairs 2557-3654.

Host Cells

Suitable host cells for the recombinant production of glycerol by the expression of G3PDH and G3P phosphatase may be either prokaryotic or eukaryotic and will be limited only by their ability to express active enzymes. Preferred host cells will be those bacteria, yeasts, and filamentous fungi typically useful for the production of glycerol such as *Citrobacter, Enterobacter, Clostridium, Klebsiella, Aerobacter, Lactobacillus, Aspergillus, Saccharomyces, Schizosaccharomyces, Zygosaccharomyces, Pichia, Kluyveromyces, Candida, Hansenula, Debaryomyces, Mucor, Torulopsis, Methylobacter, Escherichia, Salmonella, Bacillus, Streptomyces* and *Pseudomonas*. Preferred in the present invention are *E. coli* and *Saccharomyces*.

Where glycerol is a key intermediate in the production of 1,3-propanediol the host cell will either have an endogenous gene encoding a protein having a dehydratase activity or will acquire such a gene through transformation. Host cells particularly suited for production of 1,3-propanediol are *Citrobacter, Enterobacter, Clostridium, Klebsiella, Aerobacter, Lactobacillus*, and *Salmonella*, which have endogenous genes encoding dehydratase enzymes. Additionally, host cells that lack such an endogeneous gene include *E. coli*.

Vectors and Expression Cassettes

The present invention provides a variety of vectors and transformation and expression cassettes suitable for the cloning, transformation and expression of G3PDH and G3P phosphatase into a suitable host cell. Suitable vectors will be those which are compatible with the bacterium employed. Suitable vectors can be derived, for example, from a bacteria, a virus (such as bacteriophage T7 or a M-13 derived phage), a cosmid, a yeast or a plant. Protocols for obtaining and using such vectors are known to those in the art (Sambrook et al., Molecular Cloning: A Laboratory Manual—volumes 1, 2, 3 (Cold Spring Harbor Laboratory: Cold Spring Harbor, N.Y., 1989)).

Typically, the vector or cassette contains sequences directing transcription and translation of the appropriate gene, a selectable marker, and sequences allowing autonomous replication or chromosomal integration. Suitable vectors comprise a region 5' of the gene which harbors transcriptional initiation controls and a region 3' of the DNA fragment which controls transcriptional termination. It is most preferred when both control regions are derived from genes homologous to the transformed host cell. Such control regions need not be derived from the genes native to the specific species chosen as a production host.

Initiation control regions, or promoters, which are useful to drive expression of the G3PDH and G3P phosphatase genes in the desired host cell are numerous and familiar to those skilled in the art. Virtually any promoter capable of driving these genes is suitable for the present invention including but not limited to CYC1, HIS3, GAL1, GAL10, ADH1, PGK, PHO5, GAPDH, ADC1, TRP1, URA3, LEU2, ENO, and TPI (useful for expression in *Saccharomyces*); AOX1 (useful for expression in *Pichia*); and lac, trp, $\lambda P_L$, $\lambda P_R$, T7, tac, and trc, (useful for expression in *E. coli*).

Termination control regions may also be derived from various genes native to the preferred hosts. Optionally, a termination site may be unnecessary; however, it is most preferred if included.

For effective expression of the instant enzymes, DNA encoding the enzymes are linked operably through initiation codons to selected expression control regions such that expression results in the formation of the appropriate messenger RNA.

Transformation of Suitable Hosts and Expression of G3PDH and G3P Phosphatase for The Production of Glycerol Once suitable cassettes are constructed they are used to transform appropriate host cells. Introduction of the cassette containing the genes encoding G3PDH and/or G3P phosphatase into the host cell may be accomplished by known procedures such as by transformation, e.g., using calcium-permeabilized cells, electroporation, or by transfection using a recombinant phage virus (Sambrook et al., supra).

In the present invention AH21 and DAR 1 cassettes were used to transform the *E. coli* DH5α and FM5 as fully described in the GENERAL METHODS and EXAMPLES.

Random and Site Specific Mutagenisis for Disrupting Enzyme Activities:

Enzyme pathways by which organisms metabolize glycerol are known in the art, FIG. 1. Glycerol is converted to glycerol-3-phosphate (G3P) by an ATP-dependent glycerol kinase; the G3P may then be oxidized to DHAP by G3PDH. In a second pathway, glycerol is oxidized to dihydroxyacetone (DHA) by a glycerol dehydrogenase; the DHA may then be converted to DHAP by an ATP-dependent DHA kinase. In a third pathway, glycerol is oxidized to glyceraldehyde by a glycerol dehydrogenase; the glyceraldehyde may be phosphorylated to glyceraldehyde-3-phosphate by an ATP-dependent kinase. DHAP and glyceraldehyde-3-phosphate, interconverted by the action of triosephosphate isomerase, may be further metabolized via central metabolism pathways. These pathways, by introducing by-products, are deleterious to glycerol production.

One aspect of the present invention is the ability to provide a production organism for the production of glycerol where the glycerol-converting activities of glycerol kinase and glycerol dehydrogenase have been deleted. Methods of creating deletion mutants are common and well known in the art. For example, wild type cells may be exposed to a variety of agents such as radiation or chemical mutagens and then screened for the desired phenotype. When creating mutations through radiation either ultraviolet (UV) or ionizing radiation may be used. Suitable short wave UV wavelengths for genetic mutations will fall within the range of 200 nm to 300 nm where 254 nm is preferred. UV radiation in this wavelength principally causes changes within nucleic acid sequence from guanidine and cytosine to adenine and thymidine. Since all cells have DNA repair mechanisms that would repair most UV induced mutations, agents such as caffeine and other inhibitors may be added to interrupt the repair process and maximize the number of effective mutations. Long wave UV mutations using light in the 300 nm to 400 nm range are also possible but are generally not as effective as the short wave UV light unless used in conjunction with various activators such as psoralen dyes that interact with the DNA.

Mutagenesis with chemical agents is also effective for generating mutants and commonly used substances include chemicals that affect nonreplicating DNA such as $HNO_2$ and $NH_2OH$, as well as agents that affect replicating DNA such as acridine dyes, notable for causing frameshift mutations. Specific methods for creating mutants using radiation or chemical agents are well documented in the art. See for example Thomas D. Brock in Biotechnology: *A Textbook of Industrial Microbiology*, Second Edition (1989) Sinauer Associates, Inc., Sunderland, Mass., or Deshpande, Mukund V., *Appl. Biochem. Biotechnol.*, 36, 227, (1992), herein incorporated by reference.

After mutagenesis has occurred, mutants having the desired phenotype may be selected by a variety of methods. Random screening is most common where the mutagenized cells are selected for the ability to produce the desired product or intermediate. Alternatively, selective isolation of mutants can be performed by growing a mutagenized population on selective media where only resistant colonies can develop. Methods of mutant selection are highly developed and well known in the art of industrial microbiology. See Brock, Supra., DeMancilha et al., *Food Chem.*, 14, 313, (1984).

Biological mutagenic agents which target genes randomly are well known in the art. See for example De Bruijn and Rossbach in *Methods for General and Molecular Bacteriology* (1994) American Society for Microbiology, Washington, D.C. Alternatively, provided that gene sequence is known, chromosomal gene disruption with specific deletion or replacement is achieved by homologous recombination with an appropriate plasmid. See for example Hamilton et al. (1989) *J. Bacteriol.* 171:4617-4622, Balbas et al. (1993) *Gene* 136: 211-213, Gueldener et al. (1996) *Nucleic Acids Res.* 24: 2519-2524, and Smith et al. (1996) *Methods Mol. Cell. Biol.* 5: 270-277.

It is contemplated that any of the above cited methods may be used for the deletion or inactivation of glycerol kinase and glycerol dehydrogenase activities in the preferred production organism.

Media and Carbon Substrates

Fermentation media in the present invention must contain suitable carbon substrates. Suitable substrates may include but are not limited to monosaccharides such as glucose and fructose, oligosaccharides such as lactose or sucrose, polysaccharides such as starch or cellulose or mixtures thereof and unpurified mixtures from renewable feedstocks such as cheese whey permeate, cornsteep liquor, sugar beet molasses, and barley malt. Additionally, the carbon substrate may also be one-carbon substrates such as carbon dioxide, or methanol for which metabolic conversion into key biochemical intermediates has been demonstrated.

Glycerol production from single carbon sources (e.g., methanol, formaldehyde or formate) has been reported in methylotrophic yeasts (Yamada et al. (1989), *Agric. Biol. Chem.*, 53(2):541-543) and in bacteria (Hunter et al. (1985), *Biochemistry*, 24:4148-4155). These organisms can assimilate single carbon compounds, ranging in oxidation state from methane to formate, and produce glycerol. The pathway of carbon assimilation can be through ribulose monophosphate, through serine, or through xylulose-monophosphate (Gottschalk, *Bacterial Metabolism*, Second Edition, Springer-Verlag: New York (1986)). The ribulose monophosphate pathway involves the condensation of formate with ribulose-5-phosphate to form a 6 carbon sugar that becomes fructose and eventually the three carbon product, glyceraldehyde-3-phosphate. Likewise, the serine pathway assimilates the one-carbon compound into the glycolytic pathway via methylenetetrahydrofolate.

In addition to one and two carbon substrates, methylotrophic organisms are also known to utilize a number of other carbon-containing compounds such as methylamine, glucosamine and a variety of amino acids for metabolic activity. For example, methylotrophic yeast are known to utilize the carbon from methylamine to form trehalose or glycerol (Bellion et al. (1993), *Microb. Growth C1 Compd.*, [Int. Symp.], 7th, 415-32. Editor(s): Murrell, J. Collin; Kelly, Don P. Publisher: Intercept, Andover, UK). Similarly, various species of *Candida* will metabolize alanine or oleic acid (Sulter et al. (1990), *Arch. Microbiol.*, 153(5):485-9). Hence, the source of carbon utilized in the present invention may encompass a wide variety of carbon-containing substrates and will only be limited by the choice of organism.

Although all of the above mentioned carbon substrates and mixtures thereof are suitable in the present invention, preferred carbon substrates are monosaccharides, oligosaccharides, polysaccharides, single-carbon substrates or mixtures thereof. More preferred are sugars such as glucose, fructose, sucrose, maltose, lactose and single carbon substrates such as methanol and carbon dioxide. Most preferred as a carbon substrate is glucose.

In addition to an appropriate carbon source, fermentation media must contain suitable minerals, salts, cofactors, buffers and other components, known to those skilled in the art, suitable for the growth of the cultures and promotion of the enzymatic pathway necessary for glycerol production.

Culture Conditions

Typically cells are grown at 30° C. in appropriate media. Preferred growth media are common commercially prepared media such as Luria Bertani (LB) broth, Sabouraud Dextrose (SD) broth, or Yeast medium (YM) broth. Other defined or synthetic growth media may also be used and the appropriate medium for growth of the particular microorganism will be known by one skilled in the art of microbiology or fermentation science. The use of agents known to modulate catabolite repression directly or indirectly, e.g., cyclic adenosine 3':5'-monophosphate, may also be incorporated into the reaction media. Similarly, the use of agents known to modulate enzymatic activities (e.g., sulfites, bisulfites, and alkalis) that lead to enhancement of glycerol production may be used in conjunction with or as an alternative to genetic manipulations.

Suitable pH ranges for the fermentation are between pH 5.0 to pH 9.0 where the range of pH 6.0 to pH 8.0 is preferred for the initial condition.

Reactions may be performed under aerobic or anaerobic conditions where anaerobic or microaerobic conditions are preferred.

Identification of G3PDH, Glycerol Dehydrogenase, G3P Phosphatase, and Glycerol Kinase Activities The levels of expression of the proteins G3PDH, G3P phosphatase glycerol dehydrogenase, and glycerol kinase are measured by enzyme assays. Generally, G3PDH activity and glycerol dehydrogenase activity assays rely on the spectral properties of the cosubstrate, NADH, in the DHAP conversion to G-3-P and the DHA conversion to glycerol, respectively. NADH has intrinsic UV/vis absorption and its consumption can be monitored spectrophotometrically at 340 nm. G3P phosphatase activity can be measured by any method of measuring the inorganic phosphate liberated in the reaction. The most commonly used detection method uses the visible spectroscopic determination of a blue-colored phosphomolybdate ammonium complex. Glycerol kinase activity can be measured by the detection of G3P from glycerol and ATP, for example, by NMR. Assays can be directed toward more specific characteristics of individual enzymes if necessary, for example, by the use of alternate cofactors.

Identification and Recovery of Glycerol and Other Products (e.g. 1,3-propanediol)

Glycerol and other products (e.g. 1,3-propanediol) may be identified and quantified by high performance liquid chromatography (HPLC) and gas chromatography/mass spectroscopy (GC/MS) analyses on the cell-free extracts. Preferred is a HPLC method where the fermentation media are analyzed on an analytical ion exchange column using a mobile phase of 0.01N sulfiric acid in an isocratic fashion.

Methods for the recovery of glycerol from fermentation media are known in the art. For example, glycerol can be obtained from cell media by subjecting the reaction mixture to the following sequence of steps: filtration; water removal; organic solvent extraction; and fractional distillation (U.S. Pat. No. 2,986,495).

DESCRIPTION OF THE PREFERRED EMBODIMENTS

Production of Glycerol

The present invention describes a method for the production of glycerol from a suitable carbon source utilizing a recombinant organism. Particularly suitable in the invention is a bacterial host cell, transformed with an expression cassette carrying either or both of a gene that encodes a protein having a glycerol-3-phosphate dehydrogenase activity and a gene encoding a protein having a glycerol-3-phosphatase activity. In addition to the G3PDH and G3P phosphatase genes, the host cell will contain disruptions in either or both of genes encoding endogenous glycerol kinase and glycerol dehydrogenase enzymes. The combined effect of the foreign G3PDH and G3P phosphatase genes (providing a pathway from the carbon source to glycerol) with the gene disruptions (blocking the conversion of glycerol) results in an organism that is capable of efficient and reliable glycerol production.

Although the optimal organism for glycerol production contains the above mentioned gene disruptions, glycerol production is possible with a host cell containing either one or both of the foreign G3PDH and G3P phosphatase genes in the absence of such disruptions. For example, the recombinant *E. coli* strain AA200 carrying the DAR1 gene (Example 1) was capable of producing between 0.38 g/L and 0.48 g/L of glycerol depending on fermentation parameters. Similarly, the *E. coli* DH5α, carrying and expressible GPP2 gene (Example 2), was capable of 0.2 g/L of glycerol production. Where both genes are present, (Example 3 and 4), glycerol production attained about 40 g/L. Where both genes are present in conjunction with an elimination of the endogenous glycerol kinase activity, a reduction in the conversion of glycerol may be seen (Example 8). Furthermore, the presence of glycerol dehydrogenase activity is linked to the conversion of glycerol under glucose-limited conditions; thus, it is anticipated that the elimination of glycerol dehydrogenase activity will result in the reduction of glycerol conversion (Example 8).

Production of 1,3-propanediol

The present invention may also be adapted for the production of 1,3-propanediol by utilizing recombinant organisms expressing the foreign G3PDH and/or G3P phosphatase genes and containing disruptions in the endogenous glycerol kinase and/or glycerol dehydrogenase activities. Additionally, the invention provides for the process for the production of 1,3-propanediol from a recombinant organism where multiple copies of endogeneous genes are introduced. In addition to these genetic alterations, the production cell will require the presence of a gene encoding an active dehydratase enzyme. The dehydratase enzyme activity may either be a glycerol dehydratase or a diol dehydratase. The dehydratase enzyme activity may result from either the expression of an endogenous gene or from the expression of a foreign gene transfected into the host organism. Isolation and expression of genes encoding suitable dehydratase enzymes are well known in the art and are taught by applicants in PCT/US96/06705, filed 5 Nov. 1996 and U.S. Pat. No. 5,686,276 and U.S. Pat. No. 5,633,362, hereby incorporated by reference. It will be appreciated that, as glycerol is a key intermediate in the production of 1,3-propanediol, where the host cell contains a dehydratase activity in conjunction with expressed foreign G3PDH and/or G3P phosphatase genes and in the absence of the glycerol-converting glycerol kinase or glycerol dehydrogenase activities, the cell will be particularly suited for the production of 1,3-propanediol.

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

EXAMPLES

General Methods

Procedures for phosphorylations, ligations, and transformations are well known in the art. Techniques suitable for use in the following examples may be found in Sambrook et al., *Molecular Cloning: A Laboratory Manual*, Second Edition, Cold Spring Harbor Laboratory Press (1989).

Materials and methods suitable for the maintenance and growth of bacterial cultures are well known in the art. Techniques suitable for use in the following examples may be found in *Manual of Methods for General Bacteriology* (Phillipp Gerhardt, R. G. E. Murray, Ralph N. Costilow, Eugene W. Nester, Willis A. Wood, Noel R. Krieg and G. Briggs Phillips, eds), American Society for Microbiology, Washington, DC. (1994) or in *Biotechnology: A Textbook of Industrial Microbiology* (Thomas D. Brock, Second Edition (1989) Sinauer Associates, Inc., Sunderland, Mass.). All reagents and materials used for the growth and maintenance of bacterial cells were obtained from Aldrich Chemicals (Milwaukee, Wis.), DIEFCO Laboratories (Detroit, Mich.), GIBCO/BRL (Gaithersburg, Md.), or Sigma Chemical Company (St. Louis, Mo.) unless otherwise specified.

The meaning of abbreviations is as follows: "h" means hour(s), "min" means minute(s), "sec" means second(s), "d" means day(s), "mL" means milliliters, "L" means liters.

Cell Strains

The following *Escherichia coli* strains were used for transformation and expression of G3PDH and G3P phosphatase. Strains were obtained from the *E. coli* Genetic Stock Center, ATCC, or Life Technologies (Gaithersburg, Md.).

AA200 (garB10 fhuA22 ompF627fadL701 relA1 pit-10 spoT1 tpi-1 phoM510 mcrB1) (Anderson et al., (1970), *J Gen. Microbiol.*, 62:329).

BB20 (tonA22 ΔphoA8fadL701 relA1 glpR2 glpD3 pit-10 gpsA20 spoT1 T2R) (Cronan et al., *J Bact.*, 118:598).

DH5α (deoR endA1 gyrA96 hsdR17 recA1 relA1 supE44 thi-1 Δ(lacZYA-argFV169phi80lacZΔM15 F⁻) (Woodcock et al., (1989), *Nucl. Acids Res.*, 17:3469).

FM5 *Escherichia coli* (ATCC 53911)

Identification of Glycerol

The conversion of glucose to glycerol was monitored by HPLC and/or GC. Analyses were performed using standard techniques and materials available to one of skill in the art of chromatography. One suitable method utilized a Waters Maxima 820 HPLC system using UV (210 nm) and RI detection. Samples were injected onto a Shodex SH-1011 column (8 mm×300 mm; Waters, Milford, Mass.) equipped with a Shodex SH-1011P precolumn (6 mm×50 mm), temperature-controlled at 50° C., using 0.01 N $H_2SO_4$ as mobile phase at a flow rate of 0.69 mL/min. When quantitative analysis was desired, samples were prepared with a known amount of trimethylacetic acid as an external standard. Typically, the retention times of 1,3-propanediol (RI detection), glycerol (RI detection) and glucose (RI detection) were 21.39 min, 17.03 min and 12.66 min, respectively.

Glycerol was also analyzed by GC/MS. Gas chromatography with mass spectrometry detection for separation and quantitation of glycerol was performed using a DB-WAX column (30 m, 0.32 mm I.D., 0.25 um film thickness, J & W Scientific, Folsom, Calif.) at the following conditions: injector: split, 1:15; sample volume: 1 uL; temperature profile: 150° C. intitial temperature with 30 sec hold, 40° C./min to 180° C., 20° C./min to 240° C., hold for 2.5 min. Detection: EI Mass Spectrometry (Hewlett Packard 5971, San Fernando, Calif.), quantitative SIM using ions 61 m/z and 64 m/z as target ions for glycerol and glycerol-d8, and ion 43 m/z as qualifier ion for glycerol. Glycerol-d8 was used as an internal standard.

Assay for Glycerol-3-phosphatase, G3P Phosphatase

The assay for enzyme activity was performed by incubating the extract with an organic phosphate substrate in a bis-Tris or MES and magnesium buffer, pH 6.5. The substrate used was either 1-α-glycerol phosphate, or d,l-α-glycerol phosphate. The final concentrations of the reagents in the assay are: buffer (20 mM bis-Tris or 50 mM MES); $MgCl_2$ (10 mM); and substrate (20 mM). If the total protein in the sample was low and no visible precipitation occurs with an acid quench, the sample was conveniently assayed in the cuvette. This method involved incubating an enzyme sample in a cuvette that contained 20 mM substrate (50 μL, 200 mM), 50 mM MES, 10 mM $MgCl_2$, pH 6.5 buffer. The final phosphatase assay volume was 0.5 mL. The enzyme-containing sample was added to the reaction mixture; the contents of the cuvette were mixed and then the cuvette was placed in a circulating water bath at T=37° C. for 5 to 120 min, the length of time depending on whether the phosphatase activity in the enzyme sample ranged from 2 to 0.02 U/mL. The enzymatic reaction was quenched by the addition of the acid molybdate reagent (0.4 mL). After the Fiske SubbaRow reagent (0.1 mL) and distilled water (1.5 mL) were added, the solution was mixed and allowed to develop. After 10 min, to allow full color development, the absorbance of the samples was read at 660 nm using a Cary 219 UV/Vis spectrophotometer. The amount of inorganic phosphate released was compared to a standard curve that was prepared by using a stock inorganic phosphate solution (0.65 mM) and preparing 6 standards with final inorganic phosphate concentrations ranging from 0.026 to 0.130 μmol/mL.

Spectrophotometric Assay for Glycerol 3-Phosphate Dehydrogenase (G3PDH) Activity The following procedure was used as modified below from a method published by Bell et al. (1975), *J. Biol. Chem.*, 250:7153-8. This method involved incubating an enzyme sample in a cuvette that contained 0.2 mM NADH; 2.0 mM dihydroxyacetone phosphate (DHAP), and enzyme in 0.1 M Tris/HCl, pH 7.5 buffer with 5 mM DTT,in a total volume of 1.0 mL at 30° C. The spectrophotometer was set to monitor absorbance changes at the fixed wavelength of 340 nm. The instrument was blanked on a cuvette containing buffer only. After the enzyme was added to the cuvette, an absorbance reading was taken. The first substrate, NADH (50 uL 4 mM NADH; absorbance should increase approx 1.25 AU), was added to determine the background rate. The rate should be followed for at least 3 min. The second substrate, DHAP (50 uL 40 mM DHAP), was then added and the absorbance change over time was monitored for at least 3 min to determine to determine the gross rate. G3PDH activity was defined by subtracting the background rate from the gross rate.

$^{13}$C-NMR Assay for Glycerol Kinase Activity

An appropriate amount of enzyme, typically a cell-free crude extract, was added to a reaction mixture containing 40 mM ATP, 20 mM MgSO$_4$, 21 mM uniformly $^{13}$C labelled glycerol (99%, Cambridge Isotope Laboratories), and 0.1 M Tris-HCl, pH 9 for 75 min at 25° C. The conversion of glycerol to glycerol 3-phosphate was detected by $^{13}$C-NMR (125 MHz): glycerol (63.11 ppm, d, J=41 Hz and 72.66 ppm, t, J=41 Hz); glycerol 3-phosphate (62.93 ppm, d, J=41 Hz; 65.31 ppm, br d, J=43 Hz; and 72.66 ppm, dt, J=6, 41 Hz).

NADH-linked Glycerol Dehydrogenase Assay

NADH-linked glycerol dehydrogenase activity in *E. coli* strains (gldA) was determined after protein separation by non-denaturing polyacrylamide gel electrophoresis. The conversion of glycerol plus NAD$^+$ to dihydroxyacetone plus NADH was coupled with the conversion of 3-[4,5-dimethylthiazol-2-yl]-2,5-diphenyltetrazolium bromide (MTT) to a deeply colored formazan, using phenazine methosulfate (PMS) as mediator. (Tang et al. (1997) *J. Bacteriol.* 140:182).

Electrophoresis was performed in duplicate by standard procedures using native gels (8-16% TG, 1.5 mm, 15 lane gels from Novex, San Diego, Calif.). Residual glycerol was removed from the gels by washing 3× with 50 mM Tris or potassium carbonate buffer, pH 9 for 10 min. The duplicate gels were developed, with and without glycerol (approx. 0.16 M final concentration), in 15 mL of assay solution containing 50 mM Tris or potassium carbonate, pH 9, 60 mg ammonium sulfate, 75 mg NAD$^+$, 1.5 mg MTT, and 0.5 mg PMS.

The presence or absence of NADH-linked glycerol dehydrogenase activity in *E. coli* strains (gldA) was also determined, following polyacrylamide gel electrophoresis, by reaction with polyclonal antibodies raised to purified *K. pneumoniae* glycerol dehydrogenase (dhaD).

Plasmid Construction and Strain Construction

Cloning and Expression of Glycerol 3-phosphatase for Increase of Glycerol Production in *E. coli* DH5a and FM5

The *Saccharomyces cerevisiae* chromosomeV lamda clone 6592 (Gene Bank, accession # U18813x11) was obtained from ATCC. The glycerol 3-phosphate phosphatase (GPP2) gene was cloned by cloning from the lamda clone as target DNA using synthetic primers (SEQ ID NO:16 with SEQ ID NO:17) incorporating an BamHI-RBS-XbaI site at the 5' end and a SmaI site at the 3' end. The product was subdloned into pCR-Script (Stratagene, Madison, Wis.) at the SrfI site to generate the plasmids pAH15 containing GPP2. The plasmid pAH15 contains the GPP2 gene in the inactive orientation for expression from the lac promoter in pCR-Script SK+. The BamHI-SmaI fragment from pAH15 containing the GPP2 gene was inserted into pBlueScriptII SK+ to generate plasmid pAH19. The pAH19 contains the GPP2 gene in the correct orientation for expression from the lac promoter. The XbaI-PstI fragment from pAH19 containing the GPP2 gene was inserted into pPHOX2 to create plasmid pAH21. The pAH21/DH5α is the expression plasmid.

Plasmids for the Over-expression of DAR1 in *E. coli*

DAR1 was isolated by PCR cloning from genomic *S. cerevisiae* DNA using synthetic primers (SEQ ID NO:18 with SEQ ID NO:19). Successful PCR cloning places an NcoI site at the 5' end of DAR1 where the ATG within NcoI is the DAR1 initiator methionine. At the 3' end of DAR1 a BamHI site is introduced following the translation terminator. The PCR fragments were digested with NcoI+BamHI and cloned into the same sites within the expression plasmid pTrc99A (Pharmacia, Piscataway, N.J.) to give pDAR1A.

In order to create a better ribosome binding site at the 5' end of DAR1, an SpeI-RBS-NcoI linker obtained by annealing synthetic primers (SEQ ID NO:20 with SEQ ID NO:21) was inserted into the NcoI site of pDAR1A to create pAH40. Plasmid pAH40 contains the new RBS and DAR1 gene in the correct orientation for expression from the trc promoter of pTrc99A (Pharmacia, Piscataway, N.J.). The NcoI-BamHI fragment from pDAR1A and an second set of SpeI-RBS-NcoI linker obtained by annealing synthetic primers (SEQ ID NO:22 with SEQ ID NO:23) was inserted into the SpeI-BamHI site of pBC-SK+ (Stratagene, Madison, Wis.) to create plasmid pAH42. The plasmid pAH42 contains a chloramphenicol resistant gene.

Construction of Expression Cassettes for DAR1 and GPP2

Expression cassettes for DAR1 and GPP2 were assembled from the individual DAR1 and GPP2 subdlones described above using standard molecular biology methods. The BamHI-PstI fragment from pAH19 containing the ribosomal binding site (RBS) and GPP2 gene was inserted into pAH40 to create pAH43. The BamHI-PstI fragment from pAH19 containing the RBS and GPP2 gene was inserted into pAH42 to create pAH45.

The ribosome binding site at the 5' end of GPP2 was modified as follows. A BamHI-RBS-SpeI linker, obtained by annealing synthetic primers GATCCAGGAAACAGA (SEQ ID NO:24) with CTAGTCTGTTTCCTG (SEQ ID NO:25) to the XbaI-PstI fragment from pAH19 containing the GPP2 gene, was inserted into the BamHI-PstI site of pAH440 to create pAH48. Plasmid pAH48 contains the DAR1 gene, the modified RBS, and the GPP2 gene in the correct orientation for expression from the trc promoter of pTrc99A (Pharmacia, Piscataway, N.J.).

Transformation of *E. coli*

All the plasmids described here were transformed into *E. coli* DH5α or FM5 using standard molecular biology techniques. The transformants were verified by its DNA RFLP pattern.

Example 1

Production of Glycerol from *E. coli* Transformed with G3PDH Gene

Media

Synthetic media was used for anaerobic or aerobic production of glycerol using *E. coli* cells transformed with pDAR1A. The media contained per liter 6.0 g Na$_2$HPO$_4$, 3.0 g KH$_2$PO$_4$, 1.0 g NH$_4$Cl, 0.5 g NaCl, 1 mL 20% MgSO$_4$.7H$_2$O, 8.0 g glucose, 40 mg casamino acids, 0.5 ml 1% thiamine hydrochloride, 100 mg ampicillin.

Growth Conditions

Strain AA200 harboring pDAR1A or the pTrc99A vector was grown in aerobic conditions in 50 mL of media shaking at 250 rpm in 250 mL flasks at 37° C. At $A_{600}$ 0.2-0.3 isopropylthio-β-D-galactoside was added to a final concentration of 1 mM and incubation continued for 48 h. For anaerobic growth samples of induced cells were used to fill Falcon #2054 tubes which were capped and gently mixed by rotation at 37° C. for 48 h. Glycerol production was determined by HPLC analysis of the culture supernatants. Strain pDAR1A/ AA200 produced 0.38 g/L glycerol after 48 h under anaerobic conditions, and 0.48 g/L under aerobic conditions.

Example 2

Production of Glycerol from *E. coli* Transformed with G3P Phosphatase Gene (GPP2)

Media

Synthetic phoA media was used in shake flasks to demonstrate the increase of glycerol by GPP2 expression in *E. coli*. The phoA medium contained per liter: Amisoy, 12 g; ammonium sulfate, 0.62 g; MOPS, 10.5 g; Na-citrate, 1.2 g; NaOH (1 M), 10 mL; 1 M $MgSO_4$, 12 mL; 100× trace elements, 12 mL; 50% glucose, 10 mL; 1% thiamine, 10 mL; 100 mg/mL L-proline, 10 mL; 2.5 mM $FeCl_3$, 5 mL; mixed phosphates buffer, 2 mL (5 mL 0.2 M $NaH_2PO_4$+9 mL 0.2 M $K_2HPO_4$), and pH to 7.0. The 100× traces elements for phoA medium/L contained: $ZnSO_4.7 H2O$, 0.58 g; $MnSO_4.H_2O$, 0.34 g; $CuSO_4.5 H_2O$, 0.49 g; $CoCl_2.6 H_2O$, 0.47 g; $H_3BO_3$, 0.12 g, $NaMoO_4.2 H_2O$, 0.48 g.

Shake Flasks Experiments

The strains pAH21/DH5α (containing GPP2 gene) and pPHOX2/DH5α (control) were grown in 45 mL of media (phoA media, 50 ug/mL carbenicillin, and 1 ug/mL vitamin $B_{12}$) in a 250 mL shake flask at 37° C. The cultures were grown under aerobic condition (250 rpm shaking) for 24 h. Glycerol production was determined by HPLC analysis of the culture supernatant. pAH21/DH5α produced 0.2 g/L glycerol after 24 h.

Example 3

Production of Glycerol from D-GLUCOSE using Recombinant *E. coli* Containing Both GPP2 and DAR1

Growth for demonstration of increased glycerol production by *E. coli* DH5α-containing pAH43 proceeds aerobically at 37° C. in shake-flask cultures (erlenmeyer flasks, liquid volume ⅕th of total volume).

Cultures in minimal media/1% glucose shake-flasks are started by inoculation from overnight LB/1% glucose culture with antibiotic selection. Minimal media are: filter-sterilized defined media, final pH 6.8 (HCl), contained per liter: 12.6 g $(NH4)2SO_4$, 13.7 g $K_2HPO_4$, 0.2 g yeast extract (Difco), 1 g $NaHCO_3$, 5 mg vitamin $B_{12}$, 5 mL Modified Balch's Trace-Element Solution (the composition of which can be found in *Methods for General and Molecular Bacteriology* (P. Gerhardt et al., eds, p. 158, American Society for Microbiology, Washington, D.C. (1994)). The shake-flasks are incubated at 37° C. with vigorous shaking for overnight, after which they are sampled for GC analysis of the supernatant. The pAH43/ DH5α showed glycerol production of 3.8 g/L after 24 h.

Example 4

Production of Glycerol from D-Glucose using Recombinant *E. coli* Containing Both GPP2 and DAR1

Example 4 illustrates the production of glucose from the recombinant *E. coli* DH5α/pAH48, containing both the GPP2 and DAR1 genes.

The strain DH5a/pAH48 was constructed as described above in the GENERAL METHODS.

Pre-Culture

DH5α/pAH48 were pre-cultured for seeding into a fermentation run. Components and protocols for the pre-culture are listed below.

| Pre-Culture Media | |
|---|---|
| $KH_2PO_4$ | 30.0 g/L |
| Citric acid | 2.0 g/L |
| $MgSO_4 \cdot 7H_2O$ | 2.0 g/L |
| 98% $H_2SO_4$ | 2.0 mL/L |
| Ferric ammonium citrate | 0.3 g/L |
| $CaCl_2 \cdot 2H_2O$ | 0.2 g/L |
| Yeast extract | 5.0 g/L |
| Trace metals | 5.0 mL/L |
| Glucose | 10.0 g/L |
| Carbenicillin | 100.0 mg/L |

The above media components were mixed together and the pH adjusted to 6.8 with $NH_4OH$. The media was then filter sterilized.

Trace metals were used according to the following recipe:

| | |
|---|---|
| Citric acid, monohydrate | 4.0 g/L |
| $MgSO_4 \cdot 7H_2O$ | 3.0 g/L |
| $MnSO_4 \cdot H_2O$ | 0.5 g/L |
| NaCl | 1.0 g/L |
| $FeSO4.7H_2O$ | 0.1 g/L |
| $CoCl2.6H_2O$ | 0.1 g/L |
| $CaCl_2$ | 0.1 g/L |
| $ZnSO_4 \cdot 7H_2O$ | 0.1 g/L |
| $CuSO_4 \cdot 5H_2O$ | 10 mg/L |
| $AlK(SO_4)_2 \cdot 12H_2O$ | 10 mg/L |
| $H_3BO_3$ | 10 mg/L |
| $Na_2MoO_4 \cdot 2H_2O$ | 10 mg/L |
| $NiSO4.6H_2O$ | 10 mg/L |
| $Na_2SeO_3$ | 10 mg/L |
| $Na_2WO_4 \cdot 2H_2O$ | 10 mg/L |

Cultures were started from seed culture inoculated from 50 μL frozen stock (15% glycerol as cryoprotectant) to 600 mL medium in a 2-L Erlenmeyer flask. Cultures were grown at 30° C. in a shaker at 250 rpm for approximately 12 h and then used to seed the fermenter.

| Fermentation growth | |
|---|---|
| Vessel | |
| 15-L stirred tank fermenter | |
| Medium | |
| $KH_2PO_4$ | 6.8 g/L |
| Citric acid | 2.0 g/L |
| $MgSO_4 \cdot 7H_2O$ | 2.0 g/L |

-continued

| Fermentation growth | |
|---|---|
| 98% H$_2$SO$_4$ | 2.0 mL/L |
| Ferric ammonium citrate | 0.3 g/L |
| CaCl$_2$•2H$_2$O | 0.2 g/L |
| Mazu DF204 antifoam | 1.0 mL/L |

The above components were sterilized together in the fermenter vessel. The pH was raised to 6.7 with NR$_4$OH. Yeast extract (5 g/L) and trace metals solution (5 mL/L) were added aseptically from filter sterilized stock solutions. Glucose was added from 60% feed to give final concentration of 10 g/L. Carbenicillin was added at 100 mg/L. Volume after inoculation was 6 L.

Environmental Conditions for Fermentation

The temperature was controlled at 36° C. and the air flow rate was controlled at 6 standard liters per minute. Back pressure was controlled at 0.5 bar. The agitator was set at 350 rpm. Aqueous ammonia was used to control pH at 6.7. The glucose feed (60% glucose monohydrate) rate was controlled to maintain excess glucose.

Results

The results of the fermentation run are given in Table 1.

TABLE 1

| EFT (hr) | OD550 (AU) | [Glucose] (g/L) | [Glycerol] (g/L) | Total Glucose Fed (g) | Total Glycerol Produced (g) |
|---|---|---|---|---|---|
| 0 | 0.8 | 9.3 | | 25 | |
| 6 | 4.7 | 4.0 | 2.0 | 49 | 14 |
| 8 | 5.4 | 0 | 3.6 | 71 | 25 |
| 10 | 6.7 | 0.0 | 4.7 | 116 | 33 |
| 12 | 7.4 | 2.1 | 7.0 | 157 | 49 |
| 14.2 | 10.4 | 0.3 | 10.0 | 230 | 70 |
| 16.2 | 18.1 | 9.7 | 15.5 | 259 | 106 |
| 18.2 | 12.4 | 14.5 | | 305 | |
| 20.2 | 11.8 | 17.4 | 17.7 | 353 | 119 |
| 22.2 | 11.0 | 12.6 | | 382 | |
| 24.2 | 10.8 | 6.5 | 26.6 | 404 | 178 |
| 26.2 | 10.9 | 6.8 | | 442 | |
| 28.2 | 10.4 | 10.3 | 31.5 | 463 | 216 |
| 30.2 | 10.2 | 13.1 | 30.4 | 493 | 213 |
| 32.2 | 10.1 | 8.1 | 28.2 | 512 | 196 |
| 34.2 | 10.2 | 3.5 | 33.4 | 530 | 223 |
| 36.2 | 10.1 | 5.8 | | 548 | |
| 38.2 | 9.8 | 5.1 | 36.1 | 512 | 233 |

Example 5

Engineering of Glycerol Kinase Mutants of E. coli FM5 for Production of Glycerol from Glucose Construction of Integration Plasmid for Glycerol Kinase Gene Replacement in E. coli FM5

E. coli FM5 genomic DNA was prepared using the Puregene DNA Isolation Kit (Gentra Systems, Minneapolis, Minn.). A 1.0 kb DNA fragment containing partial glpF and glycerol kinase (glpK) genes was amplified by PCR (Mullis and Faloona, Methods Enzymol., 155:335-350, 1987) from FM5 genomic DNA using primers SEQ ID NO:26 and SEQ ID NO:27. A 1.1 kb DNA fragment containing partial glpK and glpX genes was amplified by PCR from FM5 genomic DNA using primers SEQ ID NO:28 and SEQ ID NO:29. A MunI site was incorporated into primer SEQ ID NO:28. The 5' end of primer SEQ ID NO:28 was the reverse complement of primer SEQ ID NO:27 to enable subsequent overlap extension PCR. The gene splicing by overlap extension technique (Horton et al., Bio Techniques, 8:528-535, 1990) was used to generate a 2.1 kb fragment by PCR using the above two PCR fragments as templates and primers SEQ ID NO:26 and SEQ ID NO:29. This fragment represented a deletion of 0.8 kb from the central region of the 1.5 kb glpK gene. Overall, this fragment had 1.0 kb and 1.1 kb flanking regions on either side of the MunI cloning site (within the partial glpK) to allow for chromosomal gene replacement by homologous recombination.

The above 2.1 kb PCR fragment was blunt-ended (using mung bean nuclease) and cloned into the pCR-Blunt vector using the Zero Blunt PCR Cloning Kit (Invitrogen, San Diego, Calif.) to yield the 5.6 kb plasmid pRN100 containing kanamycin and Zeocin resistance genes. The 1.2 kb HincII fragment from pLoxCat1 (unpublished results), containing a chloramphenicol-resistance gene flanked by bacteriophage P1 loxP sites (Snaith et al., Gene, 166:173-174, 1995), was used to interrupt the glpK fragment in plasmid pRN100 by ligating it to MunI-digested (and blunt-ended) plasmid pRN100 to yield the 6.9 kb plasmid pRN101-1. A 376 bp fragment containing the R6K origin was amplified by PCR from the vector pGP704 (Miller and Mekalanos, J. bacteriol., 170:2575-2583, 1988) using primers SEQ ID NO:30 and SEQ ID NO:31, blunt-ended, and ligated to the 5.3 kbAsp718-AatII fragment (which was blunt-ended) from pRN101-1 to yield the 5.7 kb plasmid pRN102-1 containing kanamycin and chloramphenicol resistance genes. Substitution of the ColE1 origin region in pRN101-1 with the R6K origin to generate pRN102-1 also involved deletion of most of the Zeocin resistance gene. The host for pRN102-1 replication was E. coli SY327 (Miller and Mekalanos, J. bacteriol., 170:2575-2583, 1988) which contains the pir gene necessary for the function of the R6K origin.

Engineering of Glycerol Kinase Mutant RJF10m with Chloramphenicol Resistance Gene Interrupt E. coli FM5 was electrotransformed with the non-replicative integration plasmid pRN102-1 and transformants that were chloramphenicol-resistant (12.5 µg/mL) and kanamycin-sensitive (30 µg/mL) were further screened for glycerol non-utilization on M9 minimal medium containing 1 mM glycerol. An EcoRI digest of genomic DNA from one such mutant, RJF10m, when probed with the intact glpK gene via Southern analysis (Southern, J. Mol. Biol., 98:503-517, 1975) indicated that it was a double-crossover integrant (glpK gene replacement) since the two expected 7.9 kb and 2.0 kb bands were observed, owing to the presence of an additional EcoRI site within the chloramphenicol resistance gene. The wild-type control yielded the single expected 9.4 kb band. A $^{13}$C NMR analysis of mutant RJF10m confirmed that it was incapable of converting $^{13}$C-labeled glycerol and ATP to glycerol-3-phosphate. This glpK mutant was further analyzed by genomic PCR using primer combinations SEQ ID NO:32 and SEQ ID NO:33, SEQ ID NO:34 and SEQ ID NO:35, and SEQ ID NO:32 and SEQ ID NO:35 which yielded the expected 2.3 kb, 2.4 kb, and 4.0 kb PCR fragments respectively. The wild-type control yielded the expected 3.5 kb band with primers SEQ ID NO:32 and SEQ ID NO:35. The glpK mutant RJF10m was electrotransformed with plasmid pAH48 to allow glycerol production from glucose. The glpK mutant E. coli RJF10 m has been deposited with ATCC under the terms of the Budapest Treaty on 24 Nov. 1997.

Engineering of Glycerol Kinase Mutant RJF10 m with Chloramphenicol Resistance Gene Interrupt Removed After overnight growth on YENB medium (0.75% yeast extract, 0.8% nutrient broth) at 37° C., *E. coli* RJF10m in a water suspension was electrotransformed with plasmid pJW168 (unpublished results), which contained the bacteriophage P1 Cre recombinase gene under the control of the IPTG-inducible lacUV5 promoter, a temperature-sensitive pSC101 replicon, and an ampicillin resistance gene. Upon outgrowth in SOC medium at 30° C., transformants were selected at 30° C. (permissive temperature for pJW168 replication) on LB agar medium supplemented with carbenicillin (50 µg/mL) and IPTG (1 mM). Two serial overnight transfers of pooled colonies were carried out at 30° C. on fresh LB agar medium supplemented with carbenicillin and IPTG in order to allow excision of the chromosomal chloramphenicol resistance gene via recombination at the loxP sites mediated by the Cre recombinase (Hoess and Abremski, *J. Mol. Biol.*, 181: 351-362, 1985). Resultant colonies were replica-plated on to LB agar medium supplemented with carbenicillin and IPTG and LB agar supplemented with chloramphenicol (12.5 µg/mL) to identify colonies that were carbenicillin-resistant and chloramphenicol-sensitive indicating marker gene removal. An overnight 30° C. culture of one such colony was used to inoculate 10 mL of LB medium. Upon growth at 30° C. to OD (600 nm) of 0.6, the culture was incubated at 37° C. overnight. Several dilutions were plated on prewarmed LB agar medium and the plates incubated overnight at 42° C. (the non-permissive temperature for pJW168 replication). Resultant colonies were replica-plated on to LB agar medium and LB agar medium supplemented with carbenicillin (75 µg/mL) to identify colonies that were carbenicillin-sensitive indicating loss of plasmid pJW168. One such glpK mutant, RJF10, was further analyzed by genomic PCR using primers SEQ ID NO:32 and SEQ ID NO:35 and yielded the expected 3.0 kb band confirming marker gene excision. Glycerol non-utilization by mutant RJF10 was confirmed by lack of growth on M9 minimal medium containing 1 mM glycerol. The glpK mutant RJF10 was electrotransformed with plasmid pAH48 to allow glycerol production from glucose.

Example 6

Construction of *E. coli* Strain with GLDA Gene Knockout

The gldA gene was isolated from *E. coli* by PCR (K. B. Mullis and F. A. Faloona (1987) Meth. Enzymol. 155:335-350) using primers SEQ ID NO:36 and SEQ ID NO:37, which incorporate terminal Sph1 and Xba1 sites, respectively, and cloned (T. Maniatis 1982 Molecular Cloning. A Laboratory Manual. Cold Spring Harbor, Cold Spring Harbor, N.Y.) between the Sph1 and Xba1 sites in pUC18, to generate pKP8. pKP8 was cut at the unique Sal1 and Nco1 sites within the gldA gene, the ends flushed with Klenow and religated, resulting in a 109 bp deletion in the middle of gldA and regeneration of a unique Sal1 site, to generate pKP9. A 1.4 kb DNA fragment containing the gene conferring kanamycin resistance (kan), and including about 400 bps of DNA upstream of the translational start codon and about 100 bps of DNA downstream of the translational stop codon, was isolated from pET-28a(+) (Novagen, Madison, Wis.) by PCR using primers SEQ ID NO:38 and SEQ ID NO:39, which incorporate terminal Sal1 sites, and subcloned into the unique Sal1 site of pKP9, to generate pKP 13. A 2.1 kb DNA fragment beginning 204 bps downstream of the gldA translational start codon and ending 178 bps upstream of the gldA translational stop codon, and containing the kan insertion, was isolated from pKP13 by PCR using primers SEQ ID NO:40 and SEQ ID NO:41, which incorporate terminal Sph1 and Xba1 sites, respectively, was subdloned between the Sph1 and Xba1 sites in pMAK705 (Genencor International, Palo Alto, Calif.), to generate pMP33. *E. coli* FM5 was transformed with pMP33 and selected on 20 ug/mL kan at 30° C., which is the permissive temperature for pMAK705 replication. One colony was expanded overnight at 30° C. in liquid media supplemented with 20 ug/mL kan. Approximately 32,000 cells were plated on 20 ug/mL kan and incubated for 16 hrs at 44° C., which is the restrictive temperature for pMAK705 replication. Transformants growing at 44° C. have plasmid integrated into the chromosome, occurring at a frequency of approximately 0.0001. PCR and Southern blot (E. M. Southern 1975 *J. Mol. Biol.* 98:503-517) analyses were used to determine the nature of the chromosomal integration events in the transformants. Western blot analysis (H. Towbin, et al. (1979) *Proc. Natl. Acad. Sci.* 76:4350) was used to determine whether glycerol dehydrogenase protein, the product of gldA, is produced in the transformants. An activity assay was used to determine whether glycerol dehydrogenase activity remained in the transformants. Activity in glycerol dehydrogenase bands on native gels was determined by coupling the conversion of glycerol+NAD(+)→dihydroxyacetone+NADH to the conversion of a tetrazolium dye, MTT [3-(4,5-dimethylthiazol-2-yl)-2,5-diphenyltetrazolium bromide] to a deeply colored formazan, with phenazine methosulfate as mediator. Glycerol dehydrogenase also requires the presence of 30 mM ammonium sulfate and 100 mM Tris, pH 9 (C.-T. Tang, et al. (1997) *J. Bacteriol.* 140:182). Of 8 transformants analyzed, 6 were determined to be gld, knockouts. *E. coli* MSP33.6 has been deposited with ATCC under the terms of the Budapest Treaty on 24 Nov. 1997.

Example 7

Construction of *E. coli* Strain with GLPK and GLDA Gene Knockouts

A 1.6 kb DNA fragment containing the gldA gene, and including 228 bps of DNA upstream of the translational start codon and 220 bps of DNA downstream of the translational stop codon was isolated from *E. coli* by PCR using primers SEQ ID NO:42 and SEQ ID NO:43, which incorporate terminal Sph1 and Xba1 sites, repectively, and cloned between the Sph1 and Xba1 sites of pUC18, to generate pQN2. pQN2 was cut at the unique Sal1 and Nco1 sites within the gldA gene, the ends flushed with Klenow and religated, resulting in a 109 bp deletion in the middle of gldA and regeneration of a unique Sal1 site, to generate pQN4. A 1.2 kb DNA fragment containing the gene conferring kanamycin resistance (kan), and flanked by loxP sites was isolated from pLoxKan2 (Genecor International, Palo Alto, Calif.) as a Stu1/Xho1 fragment, the ends flushed with Klenow, and subcloned into pQN4 at the Sal1 site after flushing with Klenow, to generate pQN8. The Sph1/Xba1 fragment from pQN8 containing the kan-interupted gldA was subdloned between the Sph1 and Xba1 sites of pGP704, using *E. coli* SY327 as host, to generate pQN9. *E. coli* RJF10 (see EXAMPLE 5) was transformed with pQN9 and selected on kan. Since the pGP704 backbone cannot replicate in most *E. coli* hosts, transformants arise by integration of the plasmid, (or portions of it) into the chromosome. Double crossover integration events are determined by identifying those transformants which are kan resistant and ampicillin sensitive. PCR and Southern blot analyses are used to determine the nature of the chromosomal integration events in the transformants. Western blot analysis is used to determine whether glycerol dehydrogenase, the product of gldA, is produced in the transformants. Activity assays are used to determine whether glycerol dehydrogenase activity remains in the transformants. The kan marker is removed from the chromosome using the Cre-producing plasmid pJW168, as described in EXAMPLE 5.

Example 8

Consumption of Glycerol Produced from D-Glucose by Recombinant E. coli Containing Both GPP2 and DAR1 with and without Glycerol Kinase (GLPK) Activity EXAMPLE 8 illustrates the consumption of glycerol by the recombinant E. coli FM5/pAH48 and RJF10/pAH48. The strains FM5/pAH48 and RJF10/pAH48 were constructed as described above in the GENERAL METHODS.

Pre-Culture

FM5/pAH48 and RJF10/pAH48 were pre-cultured for seeding a fermenter in the same medium used for fermentation, or in LB supplemented with 1% glucose. Either carbenicillin or ampicillin were used (100 mg/L) for plasmid maintenance. The medium for fermentation is as described in EXAMPLE 4.

Cultures were started from frozen stocks (15% glycerol as cryoprotectant) in 600 mL medium in a 2-L Erlenmeyer flask, grown at 30° C. in a shaker at 250 rpm for approximately 12 h, and used to seed the fermenter.

Fermentation Growth

A 15-L stirred tank fermenter with 5-7 L initial volume was prepared as described in EXAMPLE 4. Either carbenicillin or ampicillin were used (100 mg/L) for plasmid maintenance.

Environmental Conditions to Evaluate Glycerol Kinase (GlpK) Activity

The temperature was controlled at 30° C. and the air flow rate controlled at 6 standard liters per minute. Back pressure was controlled at 0.5 bar. Dissolved oxygen tension was controlled at 10% by stirring. Aqueous ammonia was used to control pH at 6.7. The glucose feed (60% glucose) rate was controlled to maintain excess glucose until glycerol had accumulated to at least 25 g/L. Glucose was then depleted, resulting in the net metabolism of glycerol. Table 2 shows the resulting conversion of glycerol.

TABLE 2

Conversion of glycerol by FM5/pAH48 (wt) and RJF10/pAH48 (glpK)

| Strain | number of examples | rate of glycero consumption g/OD/hr |
|---|---|---|
| FM5/pAH48 | 2 | 0.095 ± 0.015 |
| RJF10/pAH48 | 3 | 0.021 ± 0.011 |

As is seen by the data in Table 2, the rate of glycerol consumption decreases about 4-5 fold where endogenous glycerol kinase activity is eliminated.

Environmental Conditions to Evaluate Glycerol Dehydrogenase (GldA) Activity

The temperature was controlled at 30° C. and the air flow rate controlled at 6 standard liters per minute. Back pressure was controlled at 0.5 bar. Dissolved oxygen tension was controlled at 10% by stirring. Aqueous ammonia was used to control pH at 6.7. In the first fermentation, glucose was kept in excess for the duration of the fermentation. The second fermentation was operated with no residual glucose after the first 25 hours. Samples over time from the two fermentations were taken for evaluation of GlpK and GldA activities. Table 3 summarizes RJF10/pAH48 fermentations that show the effects of GldA on selectivity for glycerol.

TABLE 3

GldA and GlpK activitities from two RJF10/pAH48 fermentations

| Fermentation | Time (hrs) | GldA | GlpK | Overall selectivity (R/R) |
|---|---|---|---|---|
| 1 | 25 | − | − | 42% |
|   | 46 | − | − | 49% |
|   | 61 | + | − | 54% |
| 2 | 25 | + | − | 41% |
|   | 46 | ++ | − | 14% |
|   | 61 | ++ | − | 12% |

As is seen by the data in Table 3, the presence of glycerol dehydrogenase (GldA) activity is linked to the conversion of glycerol under glucose-limited conditions; thus, it is anticipated that eliminating glycerol dehydrogenase activity will reduce glycerol conversion.

---

SEQUENCE LISTING (1) GENERAL INFORMATION:

(iii) NUMBER OF SEQUENCES: 25

(2) INFORMATION FOR SEQ ID NO: 1:

(i) SEQUENCE CHARACTERISTICS:
      (A) LENGTH: 1380 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO: 1:

```
CTTTAATTTT CTTTTATCTT ACTCTCCTAC ATAAGACATC AAGAAACAAT TGTATATTGT      60

ACACCCCCCC CCTCCACAAA CACAAATATT GATAATATAA AGATGTCTGC TGCTGCTGA      120

AGATTAAACT TAACTTCCGG CCACTTGAAT GCTGGTAGAA AGAGAAGTTC CTCTTCTGT     180

TCTTTGAAGG CTGCCGAAAA GCCTTTCAAG GTTACTGTGA TTGGATCTGG TAACTGGGG     240

ACTACTATTG CCAAGGTGGT TGCCGAAAAT TGTAAGGGAT ACCCAGAAGT TTTCGCTCC     300

ATAGTACAAA TGTGGGTGTT CGAAGAAGAG ATCAATGGTG AAAAATTGAC TGAAATCAT     360

AATACTAGAC ATCAAAACGT GAAATACTTG CCTGGCATCA CTCTACCCGA CAATTTGGT     420

GCTAATCCAG ACTTGATTGA TTCAGTCAAG GATGTCGACA TCATCGTTTT CAACATTCC     480

CATCAATTTT TGCCCCGTAT CTGTAGCCAA TTGAAAGGTC ATGTTGATTC ACACGTCAG     540

GCTATCTCCT GTCAAAGGG TTTTGAAGTT GGTGCTAAAG GTGTCCAATT GCTATCCTC     600

TACATCACTG AGGAACTAGG TATTCAATGT GGTGCTCTAT CTGGTGCTAA CATTGCCAC     660

GAAGTCGCTC AAGAACACTG GTCTGAAACA ACAGTTGCTT ACCACATTCC AAAGGATTT     720

AGAGGCGAGG GCAAGGACGT CGACCATAAG GTTCTAAAGG CCTTGTTCCA CAGACCTTA     780

TTCCACGTTA GTGTCATCGA AGATGTTGCT GGTATCTCCA TCTGTGGTGC TTTGAAGAA     840

GTTGTTGCCT TAGGTTGTGG TTTCGTCGAA GGTCTAGGCT GGGGTAACAA CGCTTCTGC     900

GCCATCCAAA GAGTCGGTTT GGGTGAGATC ATCAGATTCG GTCAAATGTT TTTCCCAGA     960

TCTAGAGAAG AAACATACTA CCAAGAGTCT GCTGGTGTTG CTGATTTGAT CACCACCT    1020

GCTGGTGGTA GAAACGTCAA GGTTGCTAGG CTAATGGCTA CTTCTGGTAA GGACGCCT    1080

GAATGTGAAA AGGAGTTGTT GAATGGCCAA TCCGCTCAAG GTTTAATTAC CTGCAAAG    1140

GTTCACGAAT GGTTGGAAAC ATGTGGCTCT GTCAAGACT TCCCATTATT TGAAGCCG     1200

TACCAAATCG TTTACAACAA CTACCCAATG AAGAACCTGC CGGACATGAT TGAAGAAT    1260

GATCTACATG AAGATTAGAT TTATTGGAGA AAGATAACAT ATCATACTTC CCCCACTT    1320

TTCGAGGCTC TTCTATATCA TATTCATAAA TTAGCATTAT GTCATTTCTC ATAACTAC    1380

(2) INFORMATION FOR SEQ ID NO: 2:

(i) SEQUENCE CHARACTERISTICS:
        (A) LENGTH: 2946 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 2:

GAATTCGAGC CTGAAGTGCT GATTACCTTC AGGTAGACTT CATCTTGACC CATCAACCCC      60

AGCGTCAATC CTGCAAATAC ACCACCCAGC AGCACTAGGA TGATAGAGAT AATATAGTA     120

GTGGTAACGC TTGCCTCATC ACCTACGCTA TGGCCGGAAT CGGCAACATC CCTAGAATT     180

AGTACGTGTG ATCCGGATAA CAACGGCAGT GAATATATCT TCGGTATCGT AAAGATGTG     240

TATAAGATGA TGTATACCCA ATGAGGAGCG CCTGATCGTG ACCTAGACCT TAGTGGCAA     300

AACGACATAT CTATTATAGT GGGGAGAGTT TCGTGCAAAT AACAGACGCA GCAGCAAGT     360

ACTGTGACGA TATCAACTCT TTTTTTATTA TGTAATAAGC AAACAAGCAC GAATGGGGA     420

AGCCTATGTG CAATCACCAA GGTCGTCCCT TTTTTCCCAT TGCTAATTT AGAATTTAA     480

GAAACCAAAA GAATGAAGAA AGAAAACAAA TACTAGCCCT AACCCTGACT TCGTTTCTA     540

GATAATACCC TGCTTTAATG AACGGTATGC CCTAGGGTAT ATCTCACTCT GTACGTTAC     600
```

-continued

```
AACTCCGGTT ATTTTATCGG AACATCCGAG CACCCGCGCC TTCCTCAACC CAGGCACCG        660

CCCAGGTAAC CGTGCGCGAT GAGCTAATCC TGAGCCATCA CCCACCCCAC CCGTTGATG        720

CAGCAATTCG GGAGGGCGAA AATAAAACTG GAGCAAGGAA TTACCATCAC CGTCACCAT        780

ACCATCATAT CGCCTTAGCC TCTAGCCATA GCCATCATGC AAGCGTGTAT CTTCTAAGA        840

TCAGTCATCA TCATTACCGA GTTTGTTTTC CTTCACATGA TGAAGAAGGT TTGAGTATG        900

TCGAAACAAT AAGACGACGA TGGCTCTGCC ATTGGTTATA TTACGCTTTT GCGGCGAGG        960

GCCGATGGGT TGCTGAGGGG AAGAGTGTTT AGCTTACGGA CCTATTGCCA TTGTTATT       1020

GATTAATCTA TTGTTCAGCA GCTCTTCTCT ACCCTGTCAT TCTAGTATTT TTTTTTTT       1080

TTTTTGGTTT TACTTTTTTT TCTTCTTGCC TTTTTTTCTT GTTACTTTTT TTCTAGTT       1140

TTTTCCTTCC ACTAAGCTTT TTCCTTGATT TATCCTTGGG TTCTTCTTTC TACTCCTT       1200

GATTTTTTTT TTATATATTA ATTTTTAAGT TTATGTATTT TGGTAGATTC AATTCTCT       1260

CCCTTTCCTT TTCCTTCGCT CCCCTTCCTT ATCAATGCTT GCTGTCAGAA GATTAACA       1320

ATACACATTC CTTAAGCGAA CGCATCCGGT GTTATATACT CGTCGTGCAT ATAAAATT       1380

GCCTTCAAGA TCTACTTTCC TAAGAAGATC ATTATTACAA ACACAACTGC ACTCAAAG       1440

GACTGCTCAT ACTAATATCA AACAGCACAA ACACTGTCAT GAGGACCATC CTATCAGA       1500

ATCGGACTCT GCCGTGTCAA TTGTACATTT GAAACGTGCG CCCTTCAAGG TTACAGTG       1560

TGGTTCTGGT AACTGGGGGA CCACCATCGC CAAAGTCATT GCGGAAAACA CAGAATTG       1620

TTCCCATATC TTCGAGCCAG AGGTGAGAAT GTGGGTTTTT GATGAAAAGA TCGGCGAC       1680

AAATCTGACG GATATCATAA ATACAAGACA CCAGAACGTT AAATATCTAC CCAATATT       1740

CCTGCCCCAT AATCTAGTGG CCGATCCTGA TCTTTTACAC TCCATCAAGG GTGCTGAC       1800

CCTTGTTTTC AACATCCCTC ATCAATTTTT ACCAAACATA GTCAAACAAT TGCAAGGC       1860

CGTGGCCCCT CATGTAAGGG CCATCTCGTG TCTAAAAGGG TTCAGTTGG GCTCCAAG        1920

TGTGCAATTG CTATCCTCCT ATGTTACTGA TGAGTTAGGA ATCCAATGTG GCGCACTA       1980

TGGTGCAAAC TTGGCACCGG AAGTGGCCAA GGAGCATTGG TCCGAAACCA CCGTGGCT       2040

CCAACTACCA AAGGATTATC AAGGTGATGG CAAGGATGTA GATCATAAGA TTTTGAAA       2100

GCTGTTCCAC AGACCTTACT TCCACGTCAA TGTCATCGAT GATGTTGCTG GTATATCC       2160

TGCCGGTGCC TTGAAGAACG TCGTGGCACT TGCATGTGGT TTCGTAGAAG GTATGGGA       2220

GGGTAACAAT GCCTCCGCAG CCATTCAAAG GCTGGGTTTA GGTGAAATTA TCAAGTTC       2280

TAGAATGTTT TTCCCAGAAT CCAAAGTCGA GACCTACTAT CAAGAATCCG CTGGTGTT       2340

AGATCTGATC ACCACCTGCT CAGGCGGTAG AAACGTCAAG GTTGCCACAT ACATGGCC       2400

GACCGGTAAG TCAGCCTTGG AAGCAGAAAA GGAATTGCTT AACGGTCAAT CCGCCCAA       2460

GATAATCACA TGCAGAGAAG TTCACGAGTG GCTACAAACA TGTGAGTTGA CCCAAGAA       2520

CCCAATTATT CGAGGCAGTC TACCAGATAG TCTACAACAA CGTCCGCATG GAAGACCT       2580

CGGAGATGAT TGAAGAGCTA GACATCGATG ACGAATAGAC ACTCTCCCCC CCCCTCCC       2640

TCTGATCTTT CCTGTTGCCT CTTTTTCCCC CAACCAATTT ATCATTATAC ACAAGTTC       2700

CAACTACTAC TAGTAACATT ACTACAGTTA TTATAATTTT CTATTCTCTT TTTCTTTA       2760

AATCTATCAT TAACGTTAAT TTCTATATAT ACATAACTAC CATTATACAC GCTATTAT       2820

TTTACATATC ACATCACCGT TAATGAAAGA TACGACACCC TGTACACTAA CACAATTA       2880

TAATCGCCAT AACCTTTTCT GTTATCTATA GCCCTTAAAG CTGTTTCTTC GAGCTTTT       2940

CTGCAG                                                                2946
```

(2) INFORMATION FOR SEQ ID NO: 3:

(i) SEQUENCE CHARACTERISTICS:
        (A) LENGTH: 3178 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 3:

```
CTGCAGAACT TCGTCTGCTC TGTGCCCATC CTCGCGGTTA GAAAGAAGCT GAATTGTTTC      60

ATGCGCAAGG GCATCAGCGA GTGACCAATA ATCACTGCAC TAATTCCTTT TTAGCAACA      120

ATACTTATAT ACAGCACCAG ACCTTATGTC TTTTCTCTGC TCCGATACGT TATCCCACC      180

AACTTTTATT TCAGTTTTGG CAGGGGAAAT TTCACAACCC CGCACGCTAA AAATCGTAT      240

TAAACTTAAA AGAGAACAGC CACAAATAGG GAACTTTGGT CTAAACGAAG GACTCTCCC      300

CCCTTATCTT GACCGTGCTA TTGCCATCAC TGCTACAAGA CTAAATACGT ACTAATATA      360

GTTTTCGGTA ACGAGAAGAA GAGCTGCCGG TGCAGCTGCT GCCATGGCCA CAGCCACGG      420

GACGCTGTAC TGGATGACTA GCCAAGGTGA TAGGCCGTTA GTGCACAATG ACCCGAGCT      480

CATGGTGCAA TTCCCCACCG CCGCTCCACC GGCAGGTCTC TAGACGAGAC CTGCTGGAC      540

GTCTGGACAA GACGCATCAA TTCGACGTGT TGATCATCGG TGGCGGGGCC ACGGGGACA      600

GATGTGCCCT AGATGCTGCG ACCAGGGGAC TCAATGTGGC CCTTGTTGAA AAGGGGGAT      660

TTGCCTCGGG AACGTCGTCC AAATCTACCA AGATGATTCA CGGTGGGGTG CGGTACTTA      720

AGAAGGCCTT CTGGGAGTTC TCCAAGGCAC AACTGGATCT GGTCATCGAG GCACTCAAC      780

AGCGTAAACA TCTTATCAAC ACTGCCCCTC ACCTGTGCAC GGTGCTACCA ATTCTGATC      840

CCATCTACAG CACCTGGCAG GTCCCGTACA TCTATATGGG CTGTAAATTC TACGATTTC      900

TTGGCGGTTC CCAAAACTTG AAAAAATCAT ACCTACTGTC CAAATCCGCC ACCGTGGAG      960

AGGCTCCCAT GCTTACCACA GACAATTTAA AGGCCTCGCT TGTGTACCAT GATGGGTC     1020

TTAACGACTC GCGTTTGAAC GCCACTTTAG CCATCACGGG TGTGGAGAAC GGCGCTAC     1080

TCTTGATCTA TGTCGAGGTA CAAAAATTGA TCAAAGACCC AACTTCTGGT AAGGTTAT     1140

GTGCCGAGGC CCGGGACGTT GAGACTAATG AGCTTGTCAG AATCAACGCT AAATGTGT     1200

TCAATGCCAC GGGCCCATAC AGTGACGCCA TTTTGCAAAT GGACCGCAAC CCATCCGG     1260

TGCCGGACTC CCCGCTAAAC GACAACTCCA AGATCAAGTC GACTTTCAAT CAAATCTC     1320

TCATGGACCC GAAAATGGTC ATCCCATCTA TTGGCGTTCA CATCGTATTG CCCTCTTT     1380

ACTCCCCGAA GGATATGGGT TGTTGGACG TCAGAACCTC TGATGGCAGA GTGATGTT     1440

TTTTACCTTG GCAGGGCAAA GTCCTTGCCG GCACCACAGA CATCCCACTA AGCAAGT     1500

CAGAAAACCC TATGCCTACA GAGGCTGATA TTCAAGATAT CTTGAAAGAA CTACAGCA     1560

ATATCGAATT CCCCGTGAAA AGAGAAGACG TGCTAAGTGC ATGGGCTGGT GTCAGACC     1620

TGGTCAGAGA TCCACGTACA ATCCCCGCAG ACGGGAAGAA GGGCTCTGCC ACTCAGGG     1680

TGGTAAGATC CCACTTCTTG TTCACTTCGG ATAATGGCCT AATTACTATT GCAGGTGG     1740

AATGGACTAC TTACAGACAA ATGGCTGAGG AAACAGTCGA CAAAGTTGTC GAAGTTGG     1800

GATTCCACAA CCTGAAACCT TGTCACACAA GAGATATTAA GCTTGCTGGT GCAGAAGA     1860

GGACGCAAAA CTATGTGGCT TTATTGGCTC AAAACTACCA TTTATCATCA AAAATGTC     1920

ACTACTTGGT TCAAAACTAC GGAACCCGTT CCTCTATCAT TTGCGAATTT TTCAAAGA     1980
```

```
CCATGGAAAA TAAACTGCCT TTGTCCTTAG CCGACAAGGA AATAACGTA ATCTACTC      2040

GCGAGGAGAA CAACTTGGTC AATTTTGATA CTTTCAGATA TCCATTCACA ATCGGTGA      2100

TAAAGTATTC CATGCAGTAC GAATATTGTA GAACTCCCTT GGACTTCCTT TTAAGAAG      2160

CAAGATTCGC CTTCTTGGAC GCCAAGGAAG CTTTGAATGC CGTGCATGCC ACCGTCAA      2220

TTATGGGTGA TGAGTTCAAT TGGTCGGAGA AAAAGAGGCA GTGGGAACTT GAAAAAAC      2280

TGAACTTCAT CCAAGGACGT TTCGGTGTCT AAATCGATCA TGATAGTTAA GGGTGACA      2340

GATAACATTC ACAAGAGTAA TAATAATGGT AATGATGATA ATAATAATAA TGATAGTA      2400

AACAATAATA ATAATGGTGG TAATGGCAAT GAAATCGCTA TTATTACCTA TTTTCCTT      2460

TGGAAGAGTT AAAGTAAACT AAAAAAACTA CAAAATATA TGAAGAAAAA AAAAAAAA      2520

GGTAATAGAC TCTACTACTA CAATTGATCT TCAAATTATG ACCTTCCTAG TGTTTATA      2580

CTATTTCCAA TACATAATAT AATCTATATA ATCATTGCTG GTAGACTTCC GTTTTAAT      2640

CGTTTTAATT ATCCCCTTTA TCTCTAGTCT AGTTTTATCA TAAAATATAG AAACACTA      2700

TAATATTCTT CAAACGGTCC TGGTGCATAC GCAATACATA TTTATGGTGC AAAAAAAA      2760

ATGGAAAATT TTGCTAGTCA TAAACCCTTT CATAAAACAA TACGTAGACA TCGCTACT      2820

AAATTTTCAA GTTTTTATCA GATCCATGTT TCCTATCTGC CTTGACAACC TCATCGTC      2880

AATAGTACCA TTTAGAACGC CCAATATTCA CATTGTGTTC AAGGTCTTTA TTCACCAG      2940

ACGTGTAATG GCCATGATTA ATGTGCCTGT ATGGTTAACC ACTCCAAATA GCTTATAT      3000

CATAGTGTCA TTGTTTTTCA ATATAATGTT TAGTATCAAT GGATATGTTA CGACGGTG      3060

ATTTTTCTTG GTCAAATCGT AATAAAATCT CGATAAATGG ATGACTAAGA TTTTTGGT      3120

AGTTACAAAA TTTATCGTTT TCACTGTTGT CAATTTTTTG TTCTTGTAAT CACTCGAG      3178

(2) INFORMATION FOR SEQ ID NO: 4:

(i) SEQUENCE CHARACTERISTICS:
        (A) LENGTH: 816 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 4:

ATGAAACGTT TCAATGTTTT AAAATATATC AGAACAACAA AAGCAAATAT ACAAACCATC     60

GCAATGCCTT TGACCACAAA ACCTTTATCT TTGAAAATCA ACGCCGCTCT ATTCGATGT     120

GACGGTACCA TCATCATCTC TCAACCAGCC ATTGCTGCTT TCTGGAGAGA TTTCGGTAA     180

GACAAGCCTT ACTTCGATGC CGAACACGTT ATTCACATCT CTCACGGTTG GAGAACTTA    240

GATGCCATTG CCAAGTTCGC TCCAGACTTT GCTGATGAAG AATACGTTAA CAAGCTAGA    300

GGTGAAATCC CAGAAAAGTA CGGTGAACAC TCCATCGAAG TTCCAGGTGC TGTCAAGTT    360

TGTAATGCTT TGAACGCCTT GCCAAAGGAA AAATGGGCTG TCGCCACCTC TGGTACCCG    420

GACATGGCCA GAAATGGTT CGACATTTTG AAGATCAAGA GACCAGAATA CTTCATCAC    480

GCCAATGATG TCAAGCAAGG TAAGCCTCAC CCAGAACCAT ACTTAAAGGG TAGAAACGG    540

TTGGGTTTCC CAATTAATGA ACAAGACCCA TCCAAATCTA AGGTTGTTGT CTTTGAAGA    600

GCACCAGCTG GTATTGCTGC TGGTAAGGCT GCTGGCTGTA AAATCGTTGG TATTGCTAC    660

ACTTTCGATT TGGACTTCTT GAAGGAAAAG GGTTGTGACA TCATTGTCAA GAACCACGA    720

TCTATCAGAG TCGGTGAATA CAACGCTGAA ACCGATGAAG TCGAATTGAT CTTTGATGA    780
```

TACTTATACG CTAAGGATGA CTTGTTGAAA TGGTAA                                    816

(2) INFORMATION FOR SEQ ID NO: 5:

(i) SEQUENCE CHARACTERISTICS:
        (A) LENGTH: 753 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 5:

ATGGGATTGA CTACTAAACC TCTATCTTTG AAAGTTAACG CCGCTTTGTT CGACGTCGAC           60

GGTACCATTA TCATCTCTCA ACCAGCCATT GCTGCATTCT GGAGGGATTT CGGTAAGGA          120

AAACCTTATT TCGATGCTGA ACACGTTATC CAAGTCTCGC ATGGTTGGAG AACGTTTGA          180

GCCATTGCTA AGTTCGCTCC AGACTTTGCC AATGAAGAGT ATGTTAACAA ATTAGAAGC          240

GAAATTCCGG TCAAGTACGG TGAAAAATCC ATTGAAGTCC CAGGTGCAGT TAAGCTGTG          300

AACGCTTTGA ACGCTCTACC AAAAGAGAAA TGGGCTGTGG CAACTTCCGG TACCCGTGA          360

ATGGCACAAA ATGGTTCGA GCATCTGGGA ATCAGGAGAC CAAAGTACTT CATTACCGC           420

AATGATGTCA AACAGGGTAA GCCTCATCCA GAACCTATC TGAAGGGCAG GAATGGCTT           480

GGATATCCGA TCAATGAGCA AGACCCTTCC AAATCTAAGG TAGTAGTATT TGAAGACGC          540

CCAGCAGGTA TTGCCGCCGG AAAAGCCGCC GGTTGTAAGA TCATTGGTAT TGCCACTAC          600

TTCGACTTGG ACTTCCTAAA GGAAAAAGGC TGTGACATCA TTGTCAAAAA CCACGAATC          660

ATCAGAGTTG GCGGCTACAA TGCCGAAACA GACGAAGTTG AATTCATTTT TGACGACTA          720

TTATATGCTA AGGACGATCT GTTGAAATGG TAA                                      753

(2) INFORMATION FOR SEQ ID NO: 6:

(i) SEQUENCE CHARACTERISTICS:
        (A) LENGTH: 2520 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 6:

TGTATTGGCC ACGATAACCA CCCTTTGTAT ACTGTTTTTG TTTTTCACAT GGTAAATAAC           60

GACTTTTATT AAACAACGTA TGTAAAAACA TAACAAGAAT CTACCCATAC AGGCCATTT          120

GTAATTCTTC TCTTCTAATT GGAGTAAAAC CATCAATTAA AGGGTGTGGA GTAGCATAG          180

GAGGGGCTGA CTGCATTGAC AAAAAAATTG AAAAAAAAAA AGGAAAAGGA AAGGAAAAA          240

AGACAGCCAA GACTTTTAGA ACGGATAAGG TGTAATAAAA TGTGGGGGGA TGCCTGTTC          300

CGAACCATAT AAAATATACC ATGTGGTTTG AGTTGTGGCC GGAACTATAC AAATAGTTA          360

ATGTTTCCCT CTCTCTTCCG ACTTGTAGTA TTCTCCAAAC GTTACATATT CCGATCAAG          420

CAGCGCCTTT ACACTAGTTT AAAACAAGAA CAGAGCCGTA TGTCCAAAAT AATGGAAGA          480

TTACGAAGTG ACTACGTCCC GCTTATCGCC AGTATTGATG TAGGAACGAC CTCATCCAG          540

TGCATTCTGT TCAACAGATG GGGCCAGGAC GTTTCAAAAC ACCAAATTGA ATATTCAAC          600

TCAGCATCGA AGGGCAAGAT TGGGGTGTCT GGCCTAAGGA GACCCTCTAC AGCCCCAGC          660

CGTGAAACAC CAAACGCCGG TGACATCAAA ACCAGCGGAA AGCCCATCTT TTCTGCAGA          720

-continued

```
GGCTATGCCA TTCAAGAAAC CAAATTCCTA AAAATCGAGG AATTGGACTT GGACTTCCA    780
AACGAACCCA CGTTGAAGTT CCCCAAACCG GGTTGGGTTG AGTGCCATCC GCAGAAATT    840
CTGGTGAACG TCGTCCAATG CCTTGCCTCA AGTTTGCTCT CTCTGCAGAC TATCAACAG    900
GAACGTGTAG CAAACGGTCT CCCACCTTAC AAGGTAATAT GCATGGGTAT AGCAAACAT    960
AGAGAAACCA CAATTCTGTG GTCCCGCCGC ACAGGAAAAC CAATTGTTAA CTACGGTA    1020
GTTTGGAACG ACACCAGAAC GATCAAAATC GTTAGAGACA AATGGCAAAA CACTAGCG    1080
GATAGGCAAC TGCAGCTTAG ACAGAAGACT GGATTGCCAT TGCTCTCCAC GTATTTCT    1140
TGTTCCAAGC TGCGCTGGTT CCTCGACAAT GAGCCTCTGT GTACCAAGGC GTATGAGG    1200
AACGACCTGA TGTTCGGCAC TGTGGACACA TGGCTGATTT ACCAATTAAC TAAACAAA    1260
GCGTTCGTTT CTGACGTAAC CAACGCTTCC AGAACTGGAT TTATGAACCT CTCCACTT    1320
AAGTACGACA ACGAGTTGCT GGAATTTTGG GGTATTGACA AGAACCTGAT TCACATGC    1380
GAAATTGTGT CCTCATCTCA ATACTACGGT GACTTTGGCA TTCCTGATTG GATAATGG    1440
AAGCTACACG ATTCGCCAAA ACAGTACTG CGAGATCTAG TCAAGAGAAA CCTGCCCA     1500
CAGGGCTGTC TGGGCGACCA AAGCGCATCC ATGGTGGGGC AACTCGCTTA CAAACCCG    1560
GCTGCAAAAT GTACTTATGG TACCGGTTGC TTTTTACTGT ACAATACGGG GACCAAAA    1620
TTGATCTCCC AACATGGCGC ACTGACGACT CTAGCATTTT GGTTCCCACA TTTGCAAG    1680
TACGGTGGCC AAAAACCAGA ATTGAGCAAG CCACATTTTG CATTAGAGGG TTCCGTCG    1740
GTGGCTGGTG CTGTGGTCCA ATGGCTACGT GATAATTTAC GATTGATCGA TAAATCAG    1800
GATGTCGGAC CGATTGCATC TACGGTTCCT GATTCTGGTG GCGTAGTTTT CGTCCCCG    1860
TTTAGTGGCC TATTCGCTCC CTATTGGGAC CCAGATGCCA GAGCCACCAT AATGGGGA    1920
TCTCAATTCA CTACTGCCTC CCACATCGCC AGAGCTGCCG TGGAAGGTGT TTGCTTTC    1980
GCCAGGGCTA TCTTGAAGGC AATGAGTTCT GACGCGTTTG GTGAAGGTTC CAAAGACA    2040
GACTTTTTAG AGGAAATTTC CGACGTCACA TATGAAAAGT CGCCCCTGTC GGTTCTGG    2100
GTGGATGGCG GGATGTCGAG GTCTAATGAA GTCATGCAAA TTCAAGCCGA TATCCTAG    2160
CCCTGTGTCA AGTCAGAAG GTCTCCGACA GCGGAATGTA CCGCATTGGG GGCAGCCA    2220
GCAGCCAATA TGGCTTTCAA GGATGTGAAC GAGCGCCCAT TATGGAAGGA CCTACACG    2280
GTTAAGAAAT GGGTCTTTTA CAATGGAATG GAGAAAAACG AACAAATATC ACCAGAGG    2340
CATCCAAACC TTAAGATATT CAGAAGTGAA TCCGACGATG CTGAAAGGAG AAAGCATT    2400
AAGTATTGGG AAGTTGCCGT GGAAAGATCC AAAGGTTGGC TGAAGGACAT AGAAGGTG    2460
CACGAACAGG TTCTAGAAAA CTTCCAATAA CAACATAAAT AATTTCTATT AACAATGT    2520
```

(2) INFORMATION FOR SEQ ID NO: 7:

(i) SEQUENCE CHARACTERISTICS:
        (A) LENGTH: 391 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO: 7:

```
Met Ser Ala Ala Ala Asp Arg Leu Asn Leu Thr Ser Gly His Leu Asn
1               5                   10                  15
Ala Gly Arg Lys Arg Ser Ser Ser Val Ser Leu Lys Ala Ala Glu
            20                  25                  30
```

-continued

```
Lys Pro Phe Lys Val Thr Val Ile Gly Ser Gly Asn Trp Gly Thr Thr
            35                  40                  45
Ile Ala Lys Val Val Ala Glu Asn Cys Lys Gly Tyr Pro Glu Val Phe
 50                  55                  60
Ala Pro Ile Val Gln Met Trp Val Phe Glu Glu Ile Asn Gly Glu
 65                      70                  75                  80
Lys Leu Thr Glu Ile Ile Asn Thr Arg His Gln Asn Val Lys Tyr Leu
                         85                  90                  95
Pro Gly Ile Thr Leu Pro Asp Asn Leu Val Ala Asn Pro Asp Leu Ile
                100                 105                 110
Asp Ser Val Lys Asp Val Asp Ile Ile Val Phe Asn Ile Pro His Gln
            115                 120                 125
Phe Leu Pro Arg Ile Cys Ser Gln Leu Lys Gly His Val Asp Ser His
        130                 135                 140
Val Arg Ala Ile Ser Cys Leu Lys Gly Phe Glu Val Gly Ala Lys Gly
145                 150                 155                 160
Val Gln Leu Leu Ser Ser Tyr Ile Thr Glu Glu Leu Gly Ile Gln Cys
                165                 170                 175
Gly Ala Leu Ser Gly Ala Asn Ile Ala Thr Glu Val Ala Gln Glu His
            180                 185                 190
Trp Ser Glu Thr Thr Val Ala Tyr His Ile Pro Lys Asp Phe Arg Gly
        195                 200                 205
Glu Gly Lys Asp Val Asp His Lys Val Leu Lys Ala Leu Phe His Arg
210                 215                 220
Pro Tyr Phe His Val Ser Val Ile Glu Asp Val Ala Gly Ile Ser Ile
225                 230                 235                 240
Cys Gly Ala Leu Lys Asn Val Val Ala Leu Gly Cys Gly Phe Val Glu
                245                 250                 255
Gly Leu Gly Trp Gly Asn Asn Ala Ser Ala Ala Ile Gln Arg Val Gly
            260                 265                 270
Leu Gly Glu Ile Ile Arg Phe Gly Gln Met Phe Phe Pro Glu Ser Arg
        275                 280                 285
Glu Glu Thr Tyr Tyr Gln Glu Ser Ala Gly Val Ala Asp Leu Ile Thr
290                 295                 300
Thr Cys Ala Gly Gly Arg Asn Val Lys Val Ala Arg Leu Met Ala Thr
305                 310                 315                 320
Ser Gly Lys Asp Ala Trp Glu Cys Glu Lys Glu Leu Leu Asn Gly Gln
                325                 330                 335
Ser Ala Gln Gly Leu Ile Thr Cys Lys Glu Val His Glu Trp Leu Glu
            340                 345                 350
Thr Cys Gly Ser Val Glu Asp Phe Pro Leu Phe Glu Ala Val Tyr Gln
        355                 360                 365
Ile Val Tyr Asn Asn Tyr Pro Met Lys Asn Leu Pro Asp Met Ile Glu
370                 375                 380
Glu Leu Asp Leu His Glu Asp
385                 390
```

(2) INFORMATION FOR SEQ ID NO: 8:

(i) SEQUENCE CHARACTERISTICS:
        (A) LENGTH: 384 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO: 8:

```
Met Thr Ala His Thr Asn Ile Lys Gln His Lys Cys His Glu Asp
 1               5                  10                  15

His Pro Ile Arg Arg Ser Asp Ser Ala Val Ser Ile Val His Leu Lys
                20                  25                  30

Arg Ala Pro Phe Lys Val Thr Val Ile Gly Ser Gly Asn Trp Gly Thr
            35                  40                  45

Thr Ile Ala Lys Val Ile Ala Glu Asn Thr Glu Leu His Ser His Ile
50                  55                  60

Phe Glu Pro Glu Val Arg Met Trp Val Phe Asp Glu Lys Ile Gly Asp
65                  70                  75                  80

Glu Asn Leu Thr Asp Ile Ile Asn Thr Arg His Gln Asn Val Lys Tyr
                85                  90                  95

Leu Pro Asn Ile Asp Leu Pro His Asn Leu Val Ala Asp Pro Asp Leu
            100                 105                 110

Leu His Ser Ile Lys Gly Ala Asp Ile Leu Val Phe Asn Ile Pro His
        115                 120                 125

Gln Phe Leu Pro Asn Ile Val Lys Gln Leu Gln Gly His Val Ala Pro
130                 135                 140

His Val Arg Ala Ile Ser Cys Leu Lys Gly Phe Glu Leu Gly Ser Lys
145                 150                 155                 160

Gly Val Gln Leu Leu Ser Ser Tyr Val Thr Asp Glu Leu Gly Ile Gln
                165                 170                 175

Cys Gly Ala Leu Ser Gly Ala Asn Leu Ala Pro Glu Val Ala Lys Glu
            180                 185                 190

His Trp Ser Glu Thr Thr Val Ala Tyr Gln Leu Pro Lys Asp Tyr Gln
        195                 200                 205

Gly Asp Gly Lys Asp Val Asp His Lys Ile Leu Lys Leu Leu Phe His
210                 215                 220

Arg Pro Tyr Phe His Val Asn Val Ile Asp Asp Val Ala Gly Ile Ser
225                 230                 235                 240

Ile Ala Gly Ala Leu Lys Asn Val Val Ala Leu Ala Cys Gly Phe Val
                245                 250                 255

Glu Gly Met Gly Trp Gly Asn Asn Ala Ser Ala Ala Ile Gln Arg Leu
            260                 265                 270

Gly Leu Gly Glu Ile Ile Lys Phe Gly Arg Met Phe Phe Pro Glu Ser
        275                 280                 285

Lys Val Glu Thr Tyr Tyr Gln Glu Ser Ala Gly Val Ala Asp Leu Ile
290                 295                 300

Thr Thr Cys Ser Gly Gly Arg Asn Val Lys Val Ala Thr Tyr Met Ala
305                 310                 315                 320

Lys Thr Gly Lys Ser Ala Leu Glu Ala Glu Lys Glu Leu Leu Asn Gly
                325                 330                 335

Gln Ser Ala Gln Gly Ile Ile Thr Cys Arg Glu Val His Glu Trp Leu
            340                 345                 350

Gln Thr Cys Glu Leu Thr Gln Glu Phe Pro Ile Ile Arg Gly Ser Leu
        355                 360                 365

Pro Asp Ser Leu Gln Gln Arg Pro His Gly Arg Pro Thr Gly Asp Asp
370                 375                 380
```

(2) INFORMATION FOR SEQ ID NO: 9:

(i) SEQUENCE CHARACTERISTICS:

(A) LENGTH: 614 amino acids
(B) TYPE: amino acid
(C) STRANDEDNESS: unknown
(D) TOPOLOGY: unknown (ii) MOLECULE TYPE: protein (xi) SEQUENCE DESCRIPTION: SEQ ID NO: 9:

```
Met Thr Arg Ala Thr Trp Cys Asn Ser Pro Pro Leu His Arg Gln
1               5                  10                  15

Val Ser Arg Arg Asp Leu Leu Asp Arg Leu Asp Lys Thr His Gln Phe
            20                  25                  30

Asp Val Leu Ile Ile Gly Gly Gly Ala Thr Gly Thr Gly Cys Ala Leu
            35                  40                  45

Asp Ala Ala Thr Arg Gly Leu Asn Val Ala Leu Val Glu Lys Gly Asp
            50                  55                  60

Phe Ala Ser Gly Thr Ser Ser Lys Ser Thr Lys Met Ile His Gly Gly
65                  70                  75                  80

Val Arg Tyr Leu Glu Lys Ala Phe Trp Glu Phe Ser Lys Ala Gln Leu
                85                  90                  95

Asp Leu Val Ile Glu Ala Leu Asn Glu Arg Lys His Leu Ile Asn Thr
            100                 105                 110

Ala Pro His Leu Cys Thr Val Leu Pro Ile Leu Ile Pro Ile Tyr Ser
            115                 120                 125

Thr Trp Gln Val Pro Tyr Ile Tyr Met Gly Cys Lys Phe Tyr Asp Phe
            130                 135                 140

Phe Gly Gly Ser Gln Asn Leu Lys Lys Ser Tyr Leu Leu Ser Lys Ser
145                 150                 155                 160

Ala Thr Val Glu Lys Ala Pro Met Leu Thr Thr Asp Asn Leu Lys Ala
                165                 170                 175

Ser Leu Val Tyr His Asp Gly Ser Phe Asn Asp Ser Arg Leu Asn Ala
            180                 185                 190

Thr Leu Ala Ile Thr Gly Val Glu Asn Gly Ala Thr Val Leu Ile Tyr
            195                 200                 205

Val Glu Val Gln Lys Leu Ile Lys Asp Pro Thr Ser Gly Lys Val Ile
            210                 215                 220

Gly Ala Glu Ala Arg Asp Val Glu Thr Asn Glu Leu Val Arg Ile Asn
225                 230                 235                 240

Ala Lys Cys Val Val Asn Ala Thr Gly Pro Tyr Ser Asp Ala Ile Leu
                245                 250                 255

Gln Met Asp Arg Asn Pro Ser Gly Leu Pro Asp Ser Pro Leu Asn Asp
            260                 265                 270

Asn Ser Lys Ile Lys Ser Thr Phe Asn Gln Ile Ser Val Met Asp Pro
            275                 280                 285

Lys Met Val Ile Pro Ser Ile Gly Val His Ile Val Leu Pro Ser Phe
            290                 295                 300

Tyr Ser Pro Lys Asp Met Gly Leu Leu Asp Val Arg Thr Ser Asp Gly
305                 310                 315                 320

Arg Val Met Phe Phe Leu Pro Trp Gln Gly Lys Val Leu Ala Gly Thr
                325                 330                 335

Thr Asp Ile Pro Leu Lys Gln Val Pro Glu Asn Pro Met Pro Thr Glu
            340                 345                 350

Ala Asp Ile Gln Asp Ile Leu Lys Glu Leu Gln His Tyr Ile Glu Phe
            355                 360                 365

Pro Val Lys Arg Glu Asp Val Leu Ser Ala Trp Ala Gly Val Arg Pro
```

```
                370               375               380
Leu Val Arg Asp Pro Arg Thr Ile Pro Ala Asp Gly Lys Lys Gly Ser
385               390               395               400

Ala Thr Gln Gly Val Val Arg Ser His Phe Leu Phe Thr Ser Asp Asn
            405               410               415

Gly Leu Ile Thr Ile Ala Gly Gly Lys Trp Thr Thr Tyr Arg Gln Met
            420               425               430

Ala Glu Glu Thr Val Asp Lys Val Glu Val Gly Phe His Asn
            435               440               445

Leu Lys Pro Cys His Thr Arg Asp Ile Lys Leu Ala Gly Ala Glu Glu
        450               455               460

Trp Thr Gln Asn Tyr Val Ala Leu Leu Ala Gln Asn Tyr His Leu Ser
465               470               475               480

Ser Lys Met Ser Asn Tyr Leu Val Gln Asn Tyr Gly Thr Arg Ser Ser
            485               490               495

Ile Ile Cys Glu Phe Phe Lys Glu Ser Met Glu Asn Lys Leu Pro Leu
            500               505               510

Ser Leu Ala Asp Lys Glu Asn Asn Val Ile Tyr Ser Ser Glu Glu Asn
            515               520               525

Asn Leu Val Asn Phe Asp Thr Phe Arg Tyr Pro Phe Thr Ile Gly Glu
        530               535               540

Leu Lys Tyr Ser Met Gln Tyr Glu Tyr Cys Arg Thr Pro Leu Asp Phe
545               550               555               560

Leu Leu Arg Arg Thr Arg Phe Ala Phe Leu Asp Ala Lys Glu Ala Leu
            565               570               575

Asn Ala Val His Ala Thr Val Lys Val Met Gly Asp Glu Phe Asn Trp
            580               585               590

Ser Glu Lys Lys Arg Gln Trp Glu Leu Glu Lys Thr Val Asn Phe Ile
            595               600               605

Gln Gly Arg Phe Gly Val
            610

(2) INFORMATION FOR SEQ ID NO: 10:

(i) SEQUENCE CHARACTERISTICS:
        (A) LENGTH: 339 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO: 10:

Met Asn Gln Arg Asn Ala Ser Met Thr Val Ile Gly Ala Gly Ser Tyr
1               5                 10                15

Gly Thr Ala Leu Ala Ile Thr Leu Ala Arg Asn Gly His Glu Val Val
            20                25                30

Leu Trp Gly His Asp Pro Glu His Ile Ala Thr Leu Glu Arg Asp Arg
        35                40                45

Cys Asn Ala Ala Phe Leu Pro Asp Val Pro Phe Pro Asp Thr Leu His
    50                55                60

Leu Glu Ser Asp Leu Ala Thr Ala Leu Ala Ala Ser Arg Asn Ile Leu
65              70                75                80

Val Val Val Pro Ser His Val Phe Gly Glu Val Leu Arg Gln Ile Lys
            85                90                95

Pro Leu Met Arg Pro Asp Ala Arg Leu Val Trp Ala Thr Lys Gly Leu
```

```
                    100                 105                 110
Glu Ala Glu Thr Gly Arg Leu Leu Gln Asp Val Ala Arg Glu Ala Leu
                115                 120                 125

Gly Asp Gln Ile Pro Leu Ala Val Ile Ser Gly Pro Thr Phe Ala Lys
    130                 135                 140

Glu Leu Ala Ala Gly Leu Pro Thr Ala Ile Ser Leu Ala Ser Thr Asp
145                 150                 155                 160

Gln Thr Phe Ala Asp Asp Leu Gln Gln Leu Leu His Cys Gly Lys Ser
                    165                 170                 175

Phe Arg Val Tyr Ser Asn Pro Asp Phe Ile Gly Val Gln Leu Gly Gly
                180                 185                 190

Ala Val Lys Asn Val Ile Ala Ile Gly Ala Gly Met Ser Asp Gly Ile
                195                 200                 205

Gly Phe Gly Ala Asn Ala Arg Thr Ala Leu Ile Thr Arg Gly Leu Ala
    210                 215                 220

Glu Met Ser Arg Leu Gly Ala Ala Leu Gly Ala Asp Pro Ala Thr Phe
225                 230                 235                 240

Met Gly Met Ala Gly Leu Gly Asp Leu Val Leu Thr Cys Thr Asp Asn
                    245                 250                 255

Gln Ser Arg Asn Arg Arg Phe Gly Met Met Leu Gly Gln Gly Met Asp
                260                 265                 270

Val Gln Ser Ala Gln Glu Lys Ile Gly Gln Val Val Glu Gly Tyr Arg
                275                 280                 285

Asn Thr Lys Glu Val Arg Glu Leu Ala His Arg Phe Gly Val Glu Met
290                 295                 300

Pro Ile Thr Glu Glu Ile Tyr Gln Val Leu Tyr Cys Gly Lys Asn Ala
305                 310                 315                 320

Arg Glu Ala Ala Leu Thr Leu Leu Gly Arg Ala Arg Lys Asp Glu Arg
                    325                 330                 335

Ser Ser His (2) INFORMATION FOR SEQ ID NO: 11:

(i) SEQUENCE CHARACTERISTICS:
        (A) LENGTH: 501 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO: 11:

Met Glu Thr Lys Asp Leu Ile Val Ile Gly Gly Gly Ile Asn Gly Ala
1               5                   10                  15

Gly Ile Ala Ala Asp Ala Ala Gly Arg Gly Leu Ser Val Leu Met Leu
                20                  25                  30

Glu Ala Gln Asp Leu Ala Cys Ala Thr Ser Ser Ala Ser Lys Leu
                35                  40                  45        Leu

Ile His Gly Gly Leu Arg Tyr Leu Glu His Tyr Glu Phe Arg Leu Val
    50                  55                  60

Ser Glu Ala Leu Ala Glu Arg Glu Val Leu Leu Lys Met Ala Pro His
65                  70                  75                  80

Ile Ala Phe Pro Met Arg Phe Arg Leu Pro His Arg Pro His Leu Arg
                85                  90                  95

Pro Ala Trp Met Ile Arg Ile Gly Leu Phe Met Tyr Asp His Leu Gly
                100                 105                 110
```

```
Lys Arg Thr Ser Leu Pro Gly Ser Thr Gly Leu Arg Phe Gly Ala Asn
        115                 120                 125

Ser Val Leu Lys Pro Glu Ile Lys Arg Gly Phe Glu Tyr Ser Asp Cys
130                 135                 140

Trp Val Asp Asp Ala Arg Leu Val Leu Ala Asn Ala Gln Met Val Val
145                 150                 155                 160

Arg Lys Gly Gly Glu Val Leu Thr Arg Thr Arg Ala Thr Ser Ala Arg
                165                 170                 175

Arg Glu Asn Gly Leu Trp Ile Val Glu Ala Glu Asp Ile Asp Thr Gly
            180                 185                 190

Lys Lys Tyr Ser Trp Gln Ala Arg Gly Leu Val Asn Ala Thr Gly Pro
        195                 200                 205

Trp Val Lys Gln Phe Phe Asp Asp Gly Met His Leu Pro Ser Pro Tyr
    210                 215                 220

Gly Ile Arg Leu Ile Lys Gly Ser His Ile Val Val Pro Arg Val His
225                 230                 235                 240

Thr Gln Lys Gln Ala Tyr Ile Leu Gln Asn Glu Asp Lys Arg Ile Val
                245                 250                 255

Phe Val Ile Pro Trp Met Asp Glu Phe Ser Ile Ile Gly Thr Thr Asp
            260                 265                 270

Val Glu Tyr Lys Gly Asp Pro Lys Ala Val Lys Ile Glu Glu Ser Glu
        275                 280                 285

Ile Asn Tyr Leu Leu Asn Val Tyr Asn Thr His Phe Lys Lys Gln Leu
    290                 295                 300

Ser Arg Asp Asp Ile Val Trp Thr Tyr Ser Gly Val Arg Pro Leu Cys
305                 310                 315                 320

Asp Asp Glu Ser Asp Ser Pro Gln Ala Ile Thr Arg Asp Tyr Thr Leu
                325                 330                 335

Asp Ile His Asp Glu Asn Gly Lys Ala Pro Leu Leu Ser Val Phe Gly
            340                 345                 350

Gly Lys Leu Thr Thr Tyr Arg Lys Leu Ala Glu His Ala Leu Glu Lys
        355                 360                 365

Leu Thr Pro Tyr Tyr Gln Gly Ile Gly Pro Ala Trp Thr Lys Glu Ser
    370                 375                 380

Val Leu Pro Gly Gly Ala Ile Glu Gly Asp Arg Asp Asp Tyr Ala Ala
385                 390                 395                 400

Arg Leu Arg Arg Arg Tyr Pro Phe Leu Thr Glu Ser Leu Ala Arg His
                405                 410                 415

Tyr Ala Arg Thr Tyr Gly Ser Asn Ser Glu Leu Leu Leu Gly Asn Ala
            420                 425                 430

Gly Thr Val Ser Asp Leu Gly Glu Asp Phe Gly His Glu Phe Tyr Glu
        435                 440                 445

Ala Glu Leu Lys Tyr Leu Val Asp His Glu Trp Val Arg Arg Ala Asp
    450                 455                 460

Asp Ala Leu Trp Arg Arg Thr Lys Gln Gly Met Trp Leu Asn Ala Asp
465                 470                 475                 480

Gln Gln Ser Arg Val Ser Gln Trp Leu Val Glu Tyr Thr Gln Gln Arg
                485                 490                 495

Leu Ser Leu Ala Ser
            500
```

(2) INFORMATION FOR SEQ ID NO: 12:

-continued

```
    (i) SEQUENCE CHARACTERISTICS:
        (A) LENGTH: 542 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO: 12:

Met Lys Thr Arg Asp Ser Gln Ser Ser Asp Val Ile Ile Gly Gly
1               5                   10                  15

Gly Ala Thr Gly Ala Gly Ile Ala Arg Asp Cys Ala Leu Arg Gly Leu
            20                  25                  30

Arg Val Ile Leu Val Glu Arg His Asp Ile Ala Thr Gly Ala Thr Gly
            35                  40                  45

Arg Asn His Gly Leu Leu His Ser Gly Ala Arg Tyr Ala Val Thr Asp
    50                  55                  60

Ala Glu Ser Ala Arg Glu Cys Ile Ser Glu Asn Gln Ile Leu Lys Arg
65                  70                  75                  80

Ile Ala Arg His Cys Val Glu Pro Thr Asn Gly Leu Phe Ile Thr Leu
                85                  90                  95

Pro Glu Asp Asp Leu Ser Phe Gln Ala Thr Phe Ile Arg Ala Cys Glu
                100                 105                 110

Glu Ala Gly Ile Ser Ala Glu Ala Ile Asp Pro Gln Gln Ala Arg Ile
            115                 120                 125

Ile Glu Pro Ala Val Asn Pro Ala Leu Ile Gly Ala Val Lys Val Pro
130                 135                 140

Asp Gly Thr Val Asp Pro Phe Arg Leu Thr Ala Ala Asn Met Leu Asp
145                 150                 155                 160

Ala Lys Glu His Gly Ala Val Ile Leu Thr Ala His Glu Val Thr Gly
                165                 170                 175

Leu Ile Arg Glu Gly Ala Thr Val Cys Gly Val Arg Val Arg Asn His
            180                 185                 190

Leu Thr Gly Glu Thr Gln Ala Leu His Ala Pro Val Val Val Asn Ala
    195                 200                 205

Ala Gly Ile Trp Gly Gln His Ile Ala Glu Tyr Ala Asp Leu Arg Ile
210                 215                 220

Arg Met Phe Pro Ala Lys Gly Ser Leu Leu Ile Met Asp His Arg Ile
225                 230                 235                 240

Asn Gln His Val Ile Asn Arg Cys Arg Lys Pro Ser Asp Ala Asp Ile
                245                 250                 255

Leu Val Pro Gly Asp Thr Ile Ser Leu Ile Gly Thr Thr Ser Leu Arg
            260                 265                 270

Ile Asp Tyr Asn Glu Ile Asp Asn Arg Val Thr Ala Glu Glu Val
    275                 280                 285

Asp Ile Leu Leu Arg Glu Gly Glu Lys Leu Ala Pro Val Met Ala Lys
290                 295                 300

Thr Arg Ile Leu Arg Ala Tyr Ser Gly Val Arg Pro Leu Val Ala Ser
305                 310                 315                 320

Asp Asp Asp Pro Ser Gly Arg Asn Leu Ser Arg Gly Ile Val Leu Leu
                325                 330                 335

Asp His Ala Glu Arg Asp Gly Leu Asp Gly Phe Ile Thr Ile Thr Gly
            340                 345                 350

Gly Lys Leu Met Thr Tyr Arg Leu Met Ala Glu Trp Ala Thr Asp Ala
        355                 360                 365
```

```
Val Cys Arg Lys Leu Gly Asn Thr Arg Pro Cys Thr Thr Ala Asp Leu
    370                 375                 380

Ala Leu Pro Gly Ser Gln Glu Pro Ala Glu Val Thr Leu Arg Lys Val
385                 390                 395                 400

Ile Ser Leu Pro Ala Pro Leu Arg Gly Ser Ala Val Tyr Arg His Gly
                405                 410                 415

Asp Arg Thr Pro Ala Trp Leu Ser Glu Gly Arg Leu His Arg Ser Leu
                420                 425                 430

Val Cys Glu Cys Glu Ala Val Thr Ala Gly Glu Val Gln Tyr Ala Val
            435                 440                 445

Glu Asn Leu Asn Val Asn Ser Leu Leu Asp Leu Arg Arg Thr Arg
    450                 455                 460

Val Gly Met Gly Thr Cys Gln Gly Glu Leu Cys Ala Cys Arg Ala Ala
465                 470                 475                 480

Gly Leu Leu Gln Arg Phe Asn Val Thr Thr Ser Ala Gln Ser Ile Glu
                485                 490                 495

Gln Leu Ser Thr Phe Leu Asn Glu Arg Trp Lys Gly Val Gln Pro Ile
                500                 505                 510

Ala Trp Gly Asp Ala Leu Arg Glu Ser Glu Phe Thr Arg Trp Val Tyr
            515                 520                 525

Gln Gly Leu Cys Gly Leu Glu Lys Glu Gln Lys Asp Ala Leu
    530                 535                 540
```

(2) INFORMATION FOR SEQ ID NO: 13:

(i) SEQUENCE CHARACTERISTICS:
        (A) LENGTH: 250 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO: 13:

```
Met Gly Leu Thr Thr Lys Pro Leu Ser Leu Lys Val Asn Ala Ala Leu
1               5                   10                  15

Phe Asp Val Asp Gly Thr Ile Ile Ile Ser Gln Pro Ala Ile Ala Ala
                20                  25                  30

Phe Trp Arg Asp Phe Gly Lys Asp Lys Pro Tyr Phe Asp Ala Glu His
            35                  40                  45

Val Ile Gln Val Ser His Gly Trp Arg Thr Phe Asp Ala Ile Ala Lys
    50                  55                  60

Phe Ala Pro Asp Phe Ala Asn Glu Glu Tyr Val Asn Lys Leu Glu Ala
65                  70                  75                  80

Glu Ile Pro Val Lys Tyr Gly Glu Lys Ser Ile Glu Val Pro Gly Ala
                85                  90                  95

Val Lys Leu Cys Asn Ala Leu Asn Ala Leu Pro Lys Glu Lys Trp Ala
            100                 105                 110

Val Ala Thr Ser Gly Thr Arg Asp Met Ala Gln Lys Trp Phe Glu His
            115                 120                 125

Leu Gly Ile Arg Arg Pro Lys Tyr Phe Ile Thr Ala Asn Asp Val Lys
    130                 135                 140

Gln Gly Lys Pro His Pro Glu Pro Tyr Leu Lys Gly Arg Asn Gly Leu
145                 150                 155                 160

Gly Tyr Pro Ile Asn Glu Gln Asp Pro Ser Lys Ser Lys Val Val Val
                165                 170                 175
```

```
Phe Glu Asp Ala Pro Ala Gly Ile Ala Ala Gly Lys Ala Ala Gly Cys
            180                 185                 190

Lys Ile Ile Gly Ile Ala Thr Thr Phe Asp Leu Asp Phe Leu Lys Glu
            195                 200                 205

Lys Gly Cys Asp Ile Ile Val Lys Asn His Glu Ser Ile Arg Val Gly
            210                 215                 220

Gly Tyr Asn Ala Glu Thr Asp Glu Val Glu Phe Ile Phe Asp Asp Tyr
225                 230                 235                 240

Leu Tyr Ala Lys Asp Asp Leu Leu Lys Trp
                245                 250

(2) INFORMATION FOR SEQ ID NO: 14:

(i) SEQUENCE CHARACTERISTICS:
        (A) LENGTH: 271 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO: 14:

Met Lys Arg Phe Asn Val Leu Lys Tyr Ile Arg Thr Thr Lys Ala Asn
1               5                   10                  15

Ile Gln Thr Ile Ala Met Pro Leu Thr Thr Lys Pro Leu Ser Leu Lys
            20                  25                  30

Ile Asn Ala Ala Leu Phe Asp Val Asp Gly Thr Ile Ile Ile Ser Gln
            35                  40                  45

Pro Ala Ile Ala Ala Phe Trp Arg Asp Phe Gly Lys Asp Lys Pro Tyr
50                  55                  60

Phe Asp Ala Glu His Val Ile His Ile Ser His Gly Trp Arg Thr Tyr
65                  70                  75                  80

Asp Ala Ile Ala Lys Phe Ala Pro Asp Phe Ala Asp Glu Glu Tyr Val
            85                  90                  95

Asn Lys Leu Glu Gly Glu Ile Pro Glu Lys Tyr Gly Glu His Ser Ile
            100                 105                 110

Glu Val Pro Gly Ala Val Lys Leu Cys Asn Ala Leu Asn Ala Leu Pro
            115                 120                 125

Lys Glu Lys Trp Ala Val Ala Thr Ser Gly Thr Arg Asp Met Ala Lys
            130                 135                 140

Lys Trp Phe Asp Ile Leu Lys Ile Lys Arg Pro Glu Tyr Phe Ile Thr
145                 150                 155                 160

Ala Asn Asp Val Lys Gln Gly Lys Pro His Pro Glu Pro Tyr Leu Lys
            165                 170                 175

Gly Arg Asn Gly Leu Gly Phe Pro Ile Asn Glu Gln Asp Pro Ser Lys
            180                 185                 190

Ser Lys Val Val Val Phe Glu Asp Ala Pro Ala Gly Ile Ala Ala Gly
            195                 200                 205

Lys Ala Ala Gly Cys Lys Ile Val Gly Ile Ala Thr Thr Phe Asp Leu
            210                 215                 220

Asp Phe Leu Lys Glu Lys Gly Cys Asp Ile Ile Val Lys Asn His Glu
225                 230                 235                 240

Ser Ile Arg Val Gly Glu Tyr Asn Ala Glu Thr Asp Glu Val Glu Leu
            245                 250                 255

Ile Phe Asp Asp Tyr Leu Tyr Ala Lys Asp Asp Leu Leu Lys Trp
            260                 265                 270
```

(2) INFORMATION FOR SEQ ID NO: 15:

(i) SEQUENCE CHARACTERISTICS:
       (A) LENGTH: 709 amino acids
       (B) TYPE: amino acid
       (C) STRANDEDNESS: unknown
       (D) TOPOLOGY: unknown (ii) MOLECULE TYPE: protein (xi) SEQUENCE DESCRIPTION: SEQ ID NO: 15:

```
Met Phe Pro Ser Leu Phe Arg Leu Val Val Phe Ser Lys Arg Tyr Ile
1               5                   10                  15

Phe Arg Ser Ser Gln Arg Leu Tyr Thr Ser Leu Lys Gln Glu Gln Ser
            20                  25                  30

Arg Met Ser Lys Ile Met Glu Asp Leu Arg Ser Asp Tyr Val Pro Leu
        35                  40                  45

Ile Ala Ser Ile Asp Val Gly Thr Thr Ser Ser Arg Cys Ile Leu Phe
    50                  55                  60

Asn Arg Trp Gly Gln Asp Val Ser Lys His Gln Ile Glu Tyr Ser Thr
65              70                  75                  80

Ser Ala Ser Lys Gly Lys Ile Gly Val Ser Gly Leu Arg Arg Pro Ser
            85                  90                  95

Thr Ala Pro Ala Arg Glu Thr Pro Asn Ala Gly Asp Ile Lys Thr Ser
        100                 105                 110

Gly Lys Pro Ile Phe Ser Ala Glu Gly Tyr Ala Ile Gln Glu Thr Lys
    115                 120                 125

Phe Leu Lys Ile Glu Glu Leu Asp Leu Asp Phe His Asn Glu Pro Thr
130                 135                 140

Leu Lys Phe Pro Lys Pro Gly Trp Val Glu Cys His Pro Gln Lys Leu
145                 150                 155                 160

Leu Val Asn Val Val Gln Cys Leu Ala Ser Ser Leu Leu Ser Leu Gln
            165                 170                 175

Thr Ile Asn Ser Glu Arg Val Ala Asn Gly Leu Pro Pro Tyr Lys Val
        180                 185                 190

Ile Cys Met Gly Ile Ala Asn Met Arg Glu Thr Thr Ile Leu Trp Ser
    195                 200                 205

Arg Arg Thr Gly Lys Pro Ile Val Asn Tyr Gly Ile Val Trp Asn Asp
210                 215                 220

Thr Arg Thr Ile Lys Ile Val Arg Asp Lys Trp Gln Asn Thr Ser Val
225                 230                 235                 240

Asp Arg Gln Leu Gln Leu Arg Gln Lys Thr Gly Leu Pro Leu Leu Ser
            245                 250                 255

Thr Tyr Phe Ser Cys Ser Lys Leu Arg Trp Phe Leu Asp Asn Glu Pro
        260                 265                 270

Leu Cys Thr Lys Ala Tyr Glu Glu Asn Asp Leu Met Phe Gly Thr Val
    275                 280                 285

Asp Thr Trp Leu Ile Tyr Gln Leu Thr Lys Gln Lys Ala Phe Val Ser
290                 295                 300

Asp Val Thr Asn Ala Ser Arg Thr Gly Phe Met Asn Leu Ser Thr Leu
305                 310                 315                 320

Lys Tyr Asp Asn Glu Leu Leu Glu Phe Trp Gly Ile Asp Lys Asn Leu
            325                 330                 335

Ile His Met Pro Glu Ile Val Ser Ser Gln Tyr Tyr Gly Asp Phe
        340                 345                 350
```

```
Gly Ile Pro Asp Trp Ile Met Glu Lys Leu His Asp Ser Pro Lys Thr
        355                 360                 365

Val Leu Arg Asp Leu Val Lys Arg Asn Leu Pro Ile Gln Gly Cys Leu
        370                 375                 380

Gly Asp Gln Ser Ala Ser Met Val Gly Gln Leu Ala Tyr Lys Pro Gly
385                 390                 395                 400

Ala Ala Lys Cys Thr Tyr Gly Thr Gly Cys Phe Leu Leu Tyr Asn Thr
                405                 410                 415

Gly Thr Lys Lys Leu Ile Ser Gln His Gly Ala Leu Thr Thr Leu Ala
                420                 425                 430

Phe Trp Phe Pro His Leu Gln Glu Tyr Gly Gly Gln Lys Pro Glu Leu
        435                 440                 445

Ser Lys Pro His Phe Ala Leu Glu Gly Ser Val Ala Val Ala Gly Ala
        450                 455                 460

Val Val Gln Trp Leu Arg Asp Asn Leu Arg Leu Ile Asp Lys Ser Glu
465                 470                 475                 480

Asp Val Gly Pro Ile Ala Ser Thr Val Pro Asp Ser Gly Gly Val Val
                485                 490                 495

Phe Val Pro Ala Phe Ser Gly Leu Phe Ala Pro Tyr Trp Asp Pro Asp
                500                 505                 510

Ala Arg Ala Thr Ile Met Gly Met Ser Gln Phe Thr Thr Ala Ser His
        515                 520                 525

Ile Ala Arg Ala Ala Val Glu Gly Val Cys Phe Gln Ala Arg Ala Ile
        530                 535                 540

Leu Lys Ala Met Ser Ser Asp Ala Phe Gly Glu Gly Ser Lys Asp Arg
545                 550                 555                 560

Asp Phe Leu Glu Glu Ile Ser Asp Val Thr Tyr Glu Lys Ser Pro Leu
                565                 570                 575

Ser Val Leu Ala Val Asp Gly Gly Met Ser Arg Ser Asn Glu Val Met
                580                 585                 590

Gln Ile Gln Ala Asp Ile Leu Gly Pro Cys Val Lys Val Arg Arg Ser
        595                 600                 605

Pro Thr Ala Glu Cys Thr Ala Leu Gly Ala Ala Ile Ala Ala Asn Met
        610                 615                 620

Ala Phe Lys Asp Val Asn Glu Arg Pro Leu Trp Lys Asp Leu His Asp
625                 630                 635                 640

Val Lys Lys Trp Val Phe Tyr Asn Gly Met Glu Lys Asn Glu Gln Ile
                645                 650                 655

Ser Pro Glu Ala His Pro Asn Leu Lys Ile Phe Arg Ser Glu Ser Asp
                660                 665                 670

Asp Ala Glu Arg Arg Lys His Trp Lys Tyr Trp Glu Val Ala Val Glu
        675                 680                 685

Arg Ser Lys Gly Trp Leu Lys Asp Ile Glu Gly Glu His Glu Gln Val
        690                 695                 700

Leu Glu Asn Phe Gln
705

(2) INFORMATION FOR SEQ ID NO: 16:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: DNA (genomic)
```

(xi) SEQUENCE DESCRIPTION: SEQ ID NO: 16:

GCGCGGATCC AGGAGTCTAG AATTATGGGA TTGACTACTA AACCTCTATC T        51

(2) INFORMATION FOR SEQ ID NO: 17:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 17:

GATACGCCCG GGTTACCATT TCAACAGATC GTCCTT                          36

(2) INFORMATION FOR SEQ ID NO: 18:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 18:

TTGATAATAT AACCATGGCT GCTGCTGCTG ATAG                            34

(2) INFORMATION FOR SEQ ID NO: 19:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 19:

GTATGATATG TTATCTTGGA TCCAATAAAT CTAATCTTC                       39

(2) INFORMATION FOR SEQ ID NO: 20:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 20:

CATGACTAGT AAGGAGGACA ATTC                                       24

(2) INFORMATION FOR SEQ ID NO: 21:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 21:

CATGGAATTG TCCTCCTTAC TAGT                                       24

```
(2) INFORMATION FOR SEQ ID NO: 22:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 22:

CTAGTAAGGA GGACAATTC                                                   19

(2) INFORMATION FOR SEQ ID NO: 23:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 23:

CATGGAATTG TCCTCCTTA                                                   19

(2) INFORMATION FOR SEQ ID NO: 24:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(iii) HYPOTHETICAL: NO (iv) ANTI-SENSE: NO (xi) SEQUENCE DESCRIPTION: SEQ ID NO: 24:

GATCCAGGAA ACAGA                                                       15

(2) INFORMATION FOR SEQ ID NO: 25:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(iii) HYPOTHETICAL: NO (iv) ANTI-SENSE: NO (xi) SEQUENCE DESCRIPTION: SEQ ID NO: 25:

CTAGTCTGTT TCCTG                                                       15

CR-9981-A
```

What is claimed is:

1. A method for the production of glycerol from a recombinant organism comprising:
  (i) transforming a suitable host cell with
    (a) an exogenous gene encoding a protein having glycerol-3-phosphate dehydrogenase activity, and
    (b) an exogenous gene encoding a protein having glycerol-3-phosphate phosphatase activity,
    the suitable host cell having a disruption in either one or both of
    (a) an endogenous gene encoding a polypeptide having glycerol kinase activity, wherein the disruption prevents the expression of the active gene product; and
    (b) an endogenous gene encoding a polypeptide having glycerol dehydrogenase activity, wherein the disruption prevents the expression of active gene product;
  (ii) culturing the transformed host cell of (i) in the presence of at least one carbon source selected from the group consisting of monsaccharides, oligosaccharides, polysaccharides, and single-carbon substrates, whereby glycerol is produced; and
  (iii) optionally recovering the glycerol produced in (ii), and wherein the suitable host cell is selected from the group consisting of bacteria, yeast and filamentous fungi.

2. The method of claim 1 wherein the host cell contains a disruption in a gene encoding an endogenous glycerol kinase enzyme wherein the disruption prevents the expression of active gene product.

3. The method of claim 1 wherein the host cell contains a disruption in a gene encoding an endogenous glycerol dehydrogenase enzyme wherein the disruption prevents the expression of active gene product.

4. The method of claim 1 wherein the host cell contains a) a disruption in a gene encoding an endogenous glycerol kinase enzyme and b) a disruption in a gene encoding an endogenous glycerol dehydrogenase enzyme, wherein the disruptions in the respective genes prevent the expression of active gene product from either gene.

5. The method of claim 1 wherein the suitable host cell is selected from the group consisting of *Citrobacter, Enterobacter, Clostridium, Klebsiella, Aerobacter, Lactobacillus, Aspergillus, Saccharomyces, Schizosaccharomyces, Zygosaccharomyces, Pichia, Kluyveromyces, Candida, Hansenula, Debaryomyces, Mucor, Torulopsis, Methylobacter, Escherichia, Salmonella, Bacillus, Streptomyces*, and *Pseudomonas*.

6. The method of claim 5 wherein the suitable host cell is *E. coli* or *Saccharomyces* sp.

7. The method of claim 1 wherein the carbon source is glucose.

* * * * *